United States Patent
Naftalovitz et al.

(10) Patent No.: US 10,493,260 B2
(45) Date of Patent: Dec. 3, 2019

(54) ROTATING CONNECTOR

(71) Applicant: ELCAM MEDICAL AGRICULTURAL COOPERATIVE ASSOCIATION LTD.

(72) Inventors: Ziv Naftalovitz, Western Galilee (IL); Uri Rosen, Western Galilee (IL)

(73) Assignee: ELCAM MEDICAL AGRICULTURAL COOPERATIVE ASSOCIATION LTD., Kibbutz Bar-Am (IL)

( * ) Notice: Subject to any disclaimer, the term of this patent is extended or adjusted under 35 U.S.C. 154(b) by 36 days.

(21) Appl. No.: 15/563,090

(22) PCT Filed: May 26, 2016

(86) PCT No.: PCT/IL2016/050551
§ 371 (c)(1),
(2) Date: Sep. 29, 2017

(87) PCT Pub. No.: WO2016/189538
PCT Pub. Date: Dec. 1, 2016

(65) Prior Publication Data
US 2018/0071507 A1    Mar. 15, 2018

Related U.S. Application Data

(60) Provisional application No. 62/167,879, filed on May 28, 2015.

(51) Int. Cl.
*A61M 25/16* (2006.01)
*A61M 25/18* (2006.01)
(Continued)

(52) U.S. Cl.
CPC ........ *A61M 39/1055* (2013.01); *A61M 39/10* (2013.01); *A61M 39/1011* (2013.01); *A61M 39/12* (2013.01); *A61M 2205/583* (2013.01)

(58) Field of Classification Search
CPC ............ A61M 2205/583; A61M 39/10; A61M 39/1011; A61M 39/1055; A61M 39/12; A61M 5/145
See application file for complete search history.

(56) References Cited

U.S. PATENT DOCUMENTS 8,777,931 B2 *   7/2014   Davis .................... A61M 39/10
                                                                604/533
2006/0033331 A1   2/2006   Ziman
(Continued)

FOREIGN PATENT DOCUMENTS

EP       1 784 600 A2    5/2007
EP       2 482 916 A1    8/2012
(Continued)

*Primary Examiner* — Rebecca E Eisenberg
(74) *Attorney, Agent, or Firm* — Sughrue Mion, PLLC

(57) ABSTRACT

A rotatable fluid flow connector including a base element and a rotatable element, the rotatable element being non-removably but rotatably connected to the base element for rotation about a common axis. For use in a rotatable fluid flow connector including a base element, a rotatable element arranged for locking engagement with the base element and rotation with respect thereto about a common axis, the rotatable element being formed with a flange having at least one flange surface extending in a plane which is perpendicular to the common axis.

20 Claims, 43 Drawing Sheets

(51) Int. Cl.
  *A61M 39/00* (2006.01)
  *A61M 39/10* (2006.01)
  *A61M 39/12* (2006.01)

(56) References Cited

U.S. PATENT DOCUMENTS

| | | |
|---|---|---|
| 2008/0103485 A1 | 5/2008 | Kruger |
| 2008/0172039 A1 | 7/2008 | Raines |
| 2008/0287920 A1 | 11/2008 | Fangrow et al. |
| 2011/0284561 A1 | 11/2011 | Rosenquist et al. |
| 2012/0209057 A1 | 8/2012 | Siess et al. |
| 2013/0245612 A1 | 9/2013 | Ziman |
| 2013/0331692 A1 | 12/2013 | Mouri |
| 2014/0243797 A1 | 8/2014 | Jensen et al. |
| 2014/0265319 A1 | 9/2014 | Clark et al. |
| 2014/0276651 A1 | 9/2014 | Schultz |
| 2014/0332091 A1 | 11/2014 | Ueda et al. |
| 2015/0001845 A1 | 1/2015 | Penny et al. |
| 2015/0005715 A1 | 1/2015 | Cowan et al. |
| 2015/0040898 A1 | 2/2015 | Breckon |
| 2015/0126958 A1 | 5/2015 | Sanders et al. |

FOREIGN PATENT DOCUMENTS

| | | |
|---|---|---|
| EP | 2 599 519 A1 | 6/2013 |
| EP | 2 731 666 A1 | 5/2014 |
| EP | 2 814 560 A1 | 12/2014 |
| EP | 2 823 208 A1 | 1/2015 |
| EP | 2 552 516 B1 | 1/2017 |
| JP | 2014-39847 A | 3/2014 |
| JP | 2014-208283 A | 11/2014 |
| WO | 2011/156521 A2 | 12/2011 |
| WO | 2013/028273 A1 | 2/2013 |
| WO | 2013/036854 A1 | 3/2013 |
| WO | 2014/074929 A1 | 5/2014 |
| WO | 2014/133826 A1 | 9/2014 |
| WO | 2014/159313 A1 | 10/2014 |
| WO | 2015/069631 A1 | 5/2015 |

\* cited by examiner

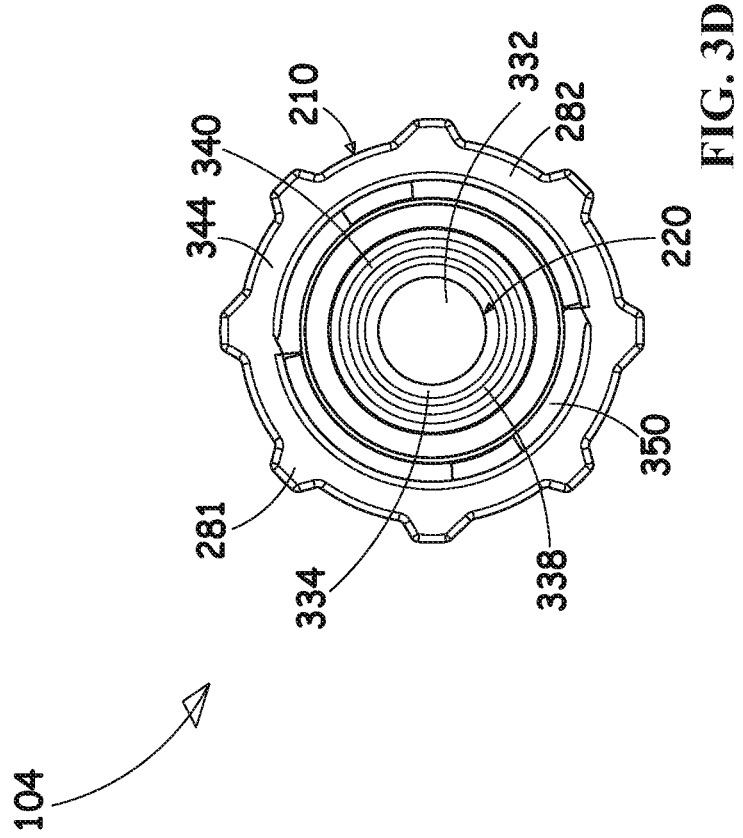

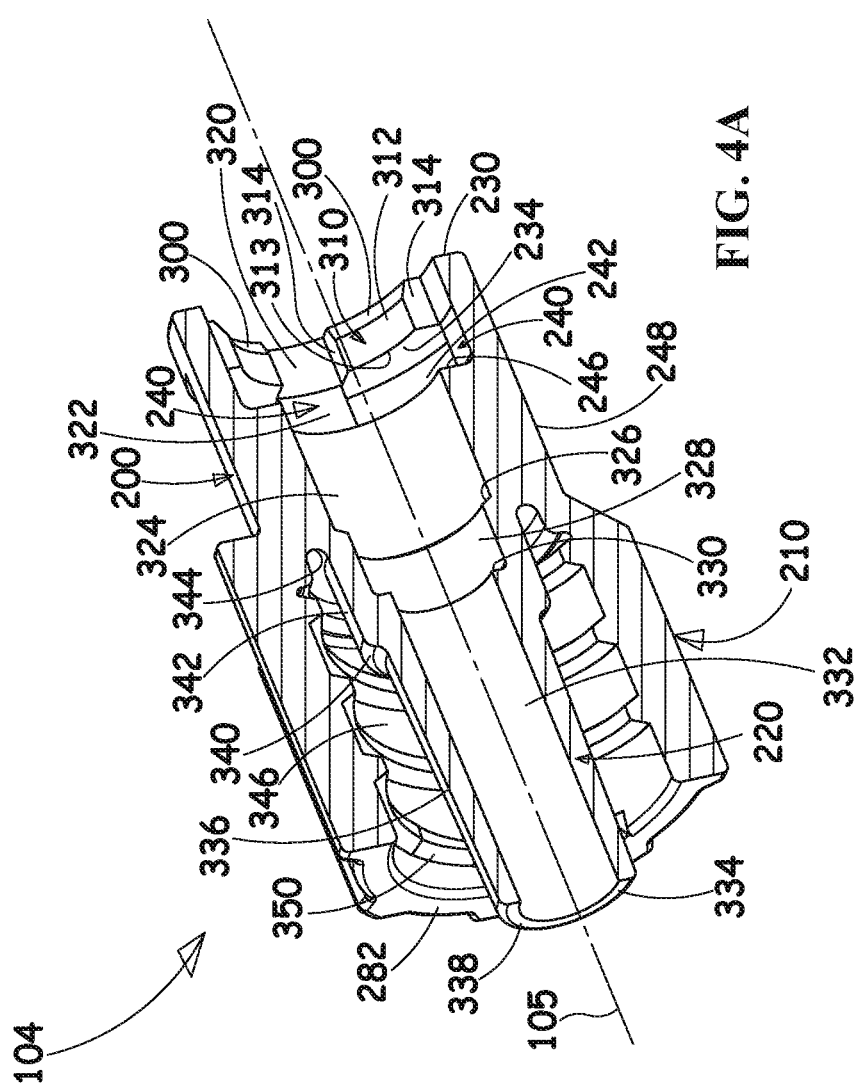

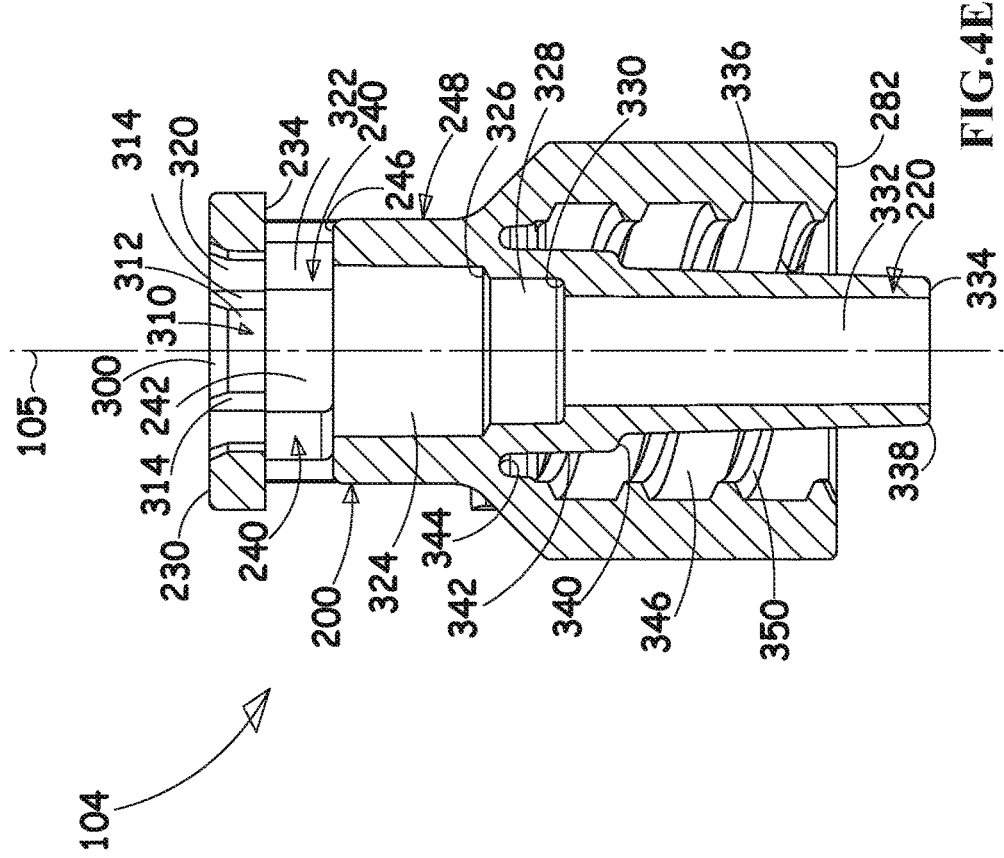

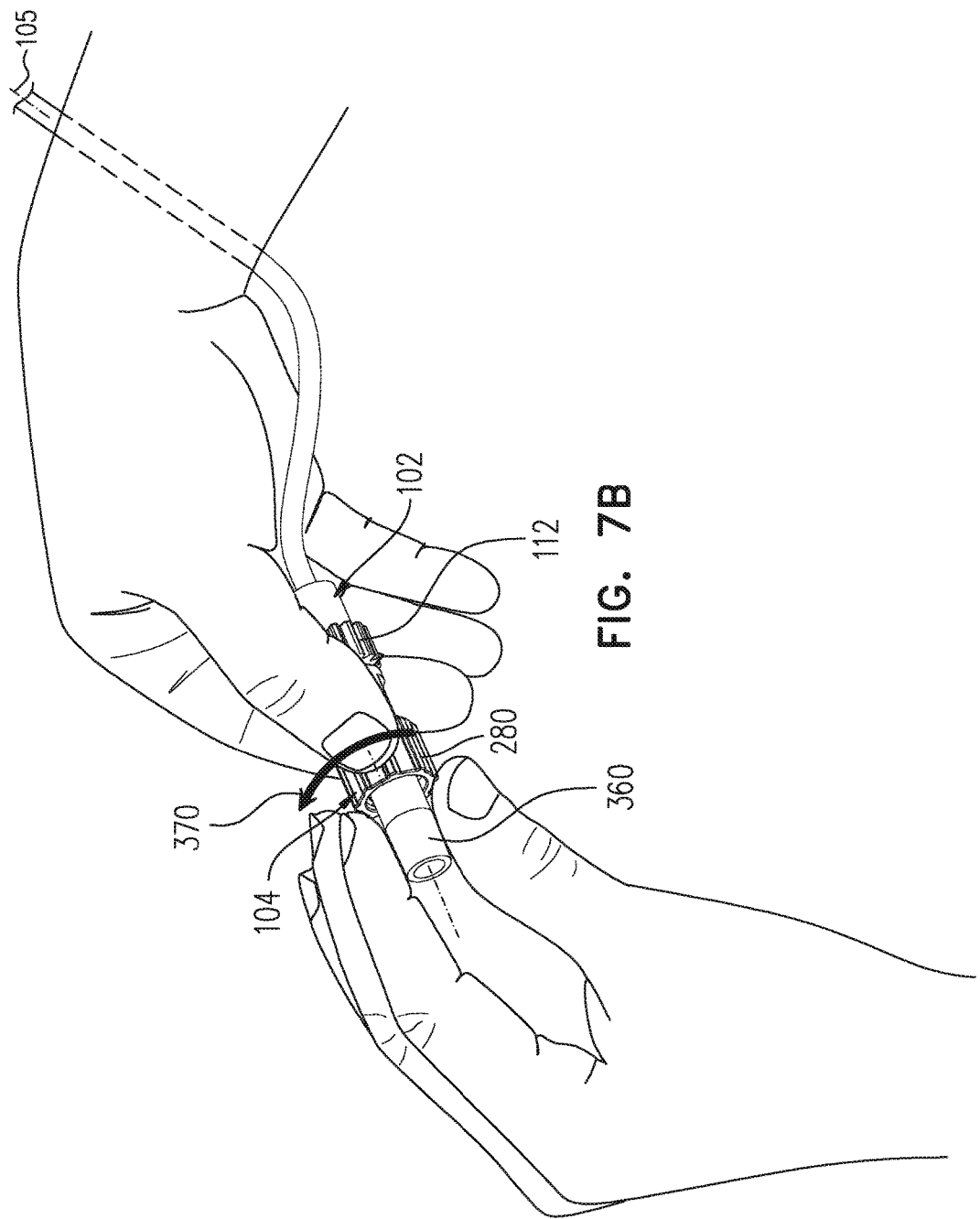

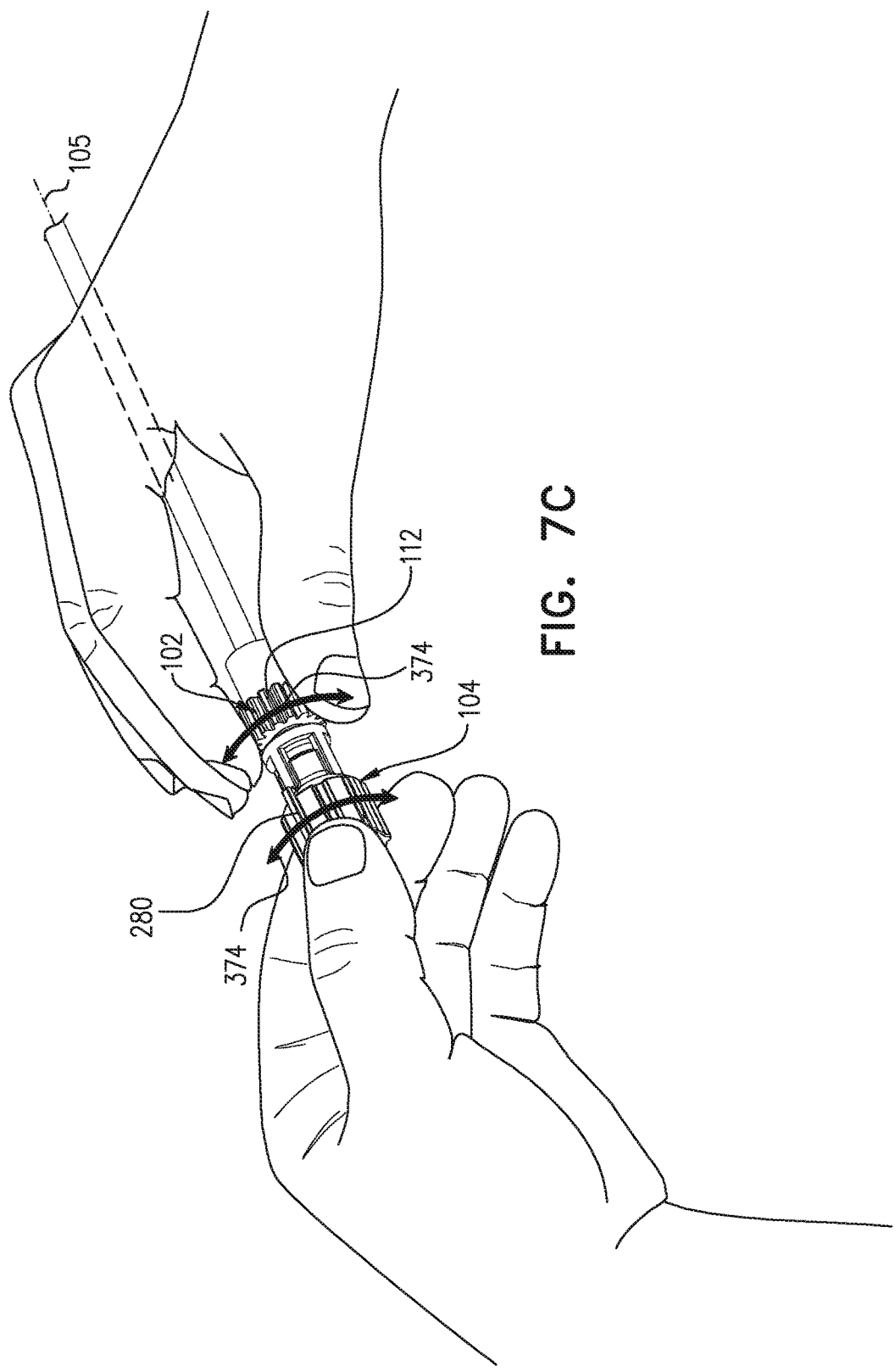

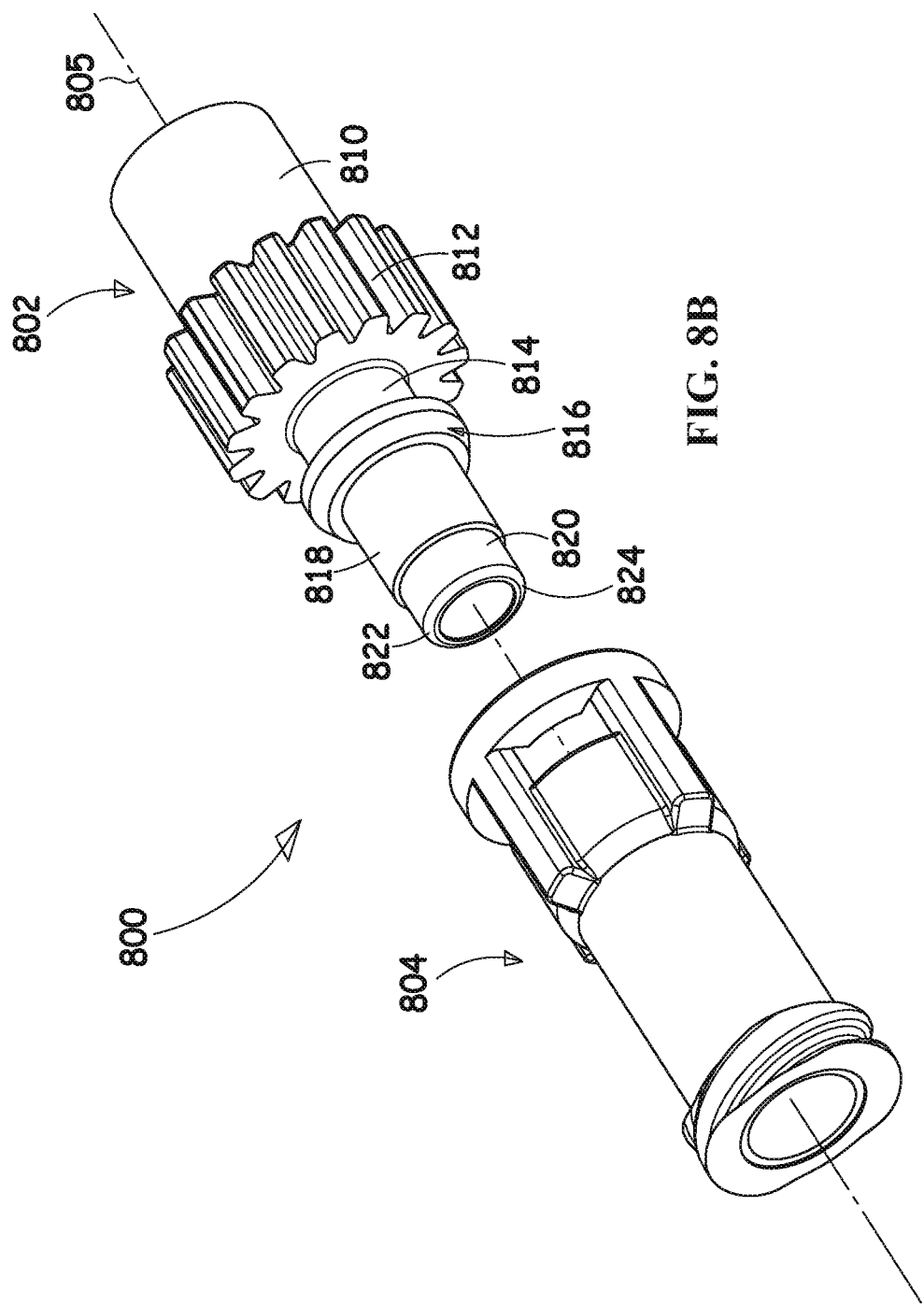

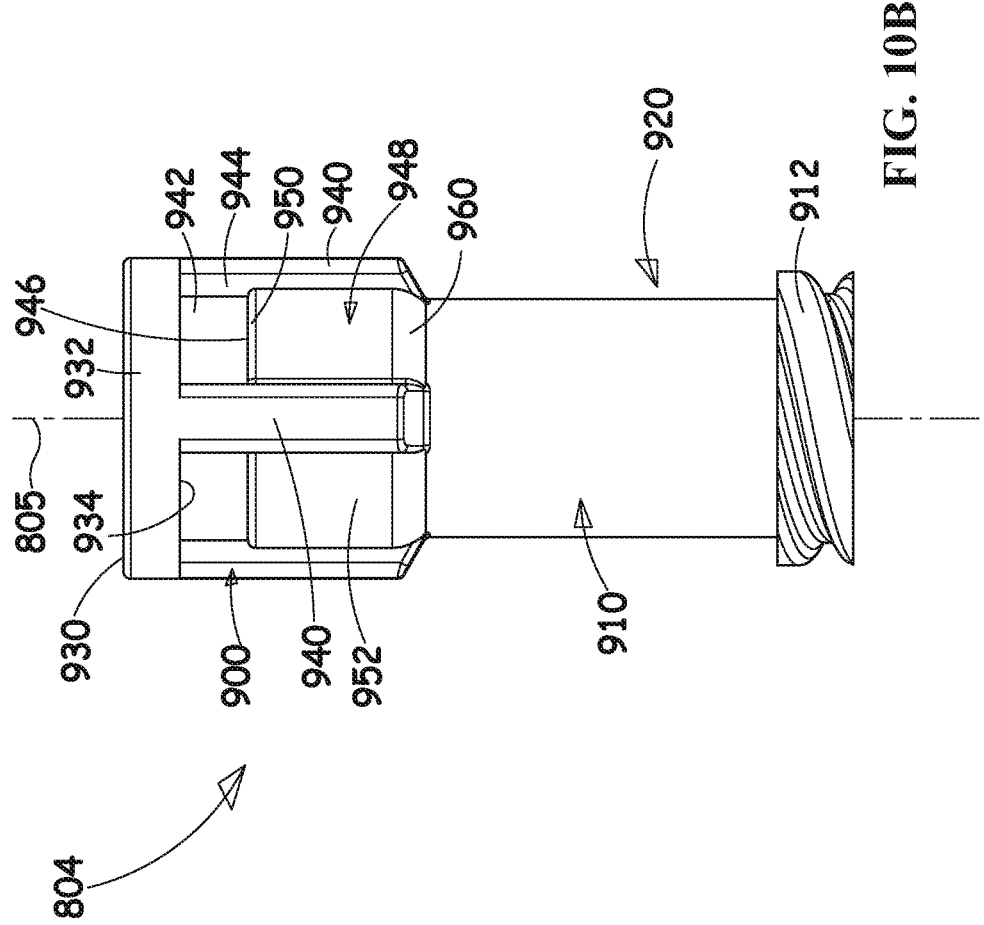

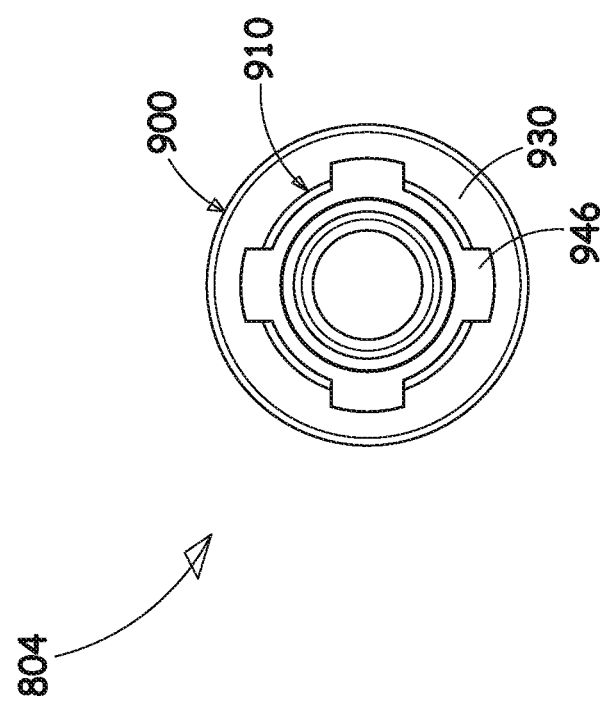

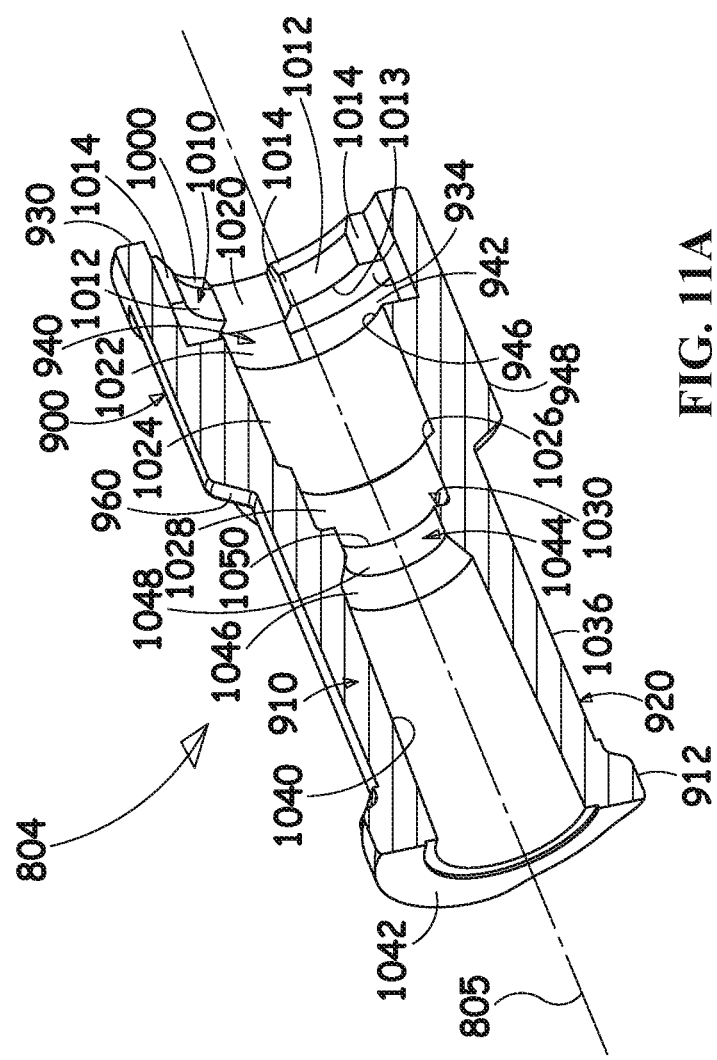

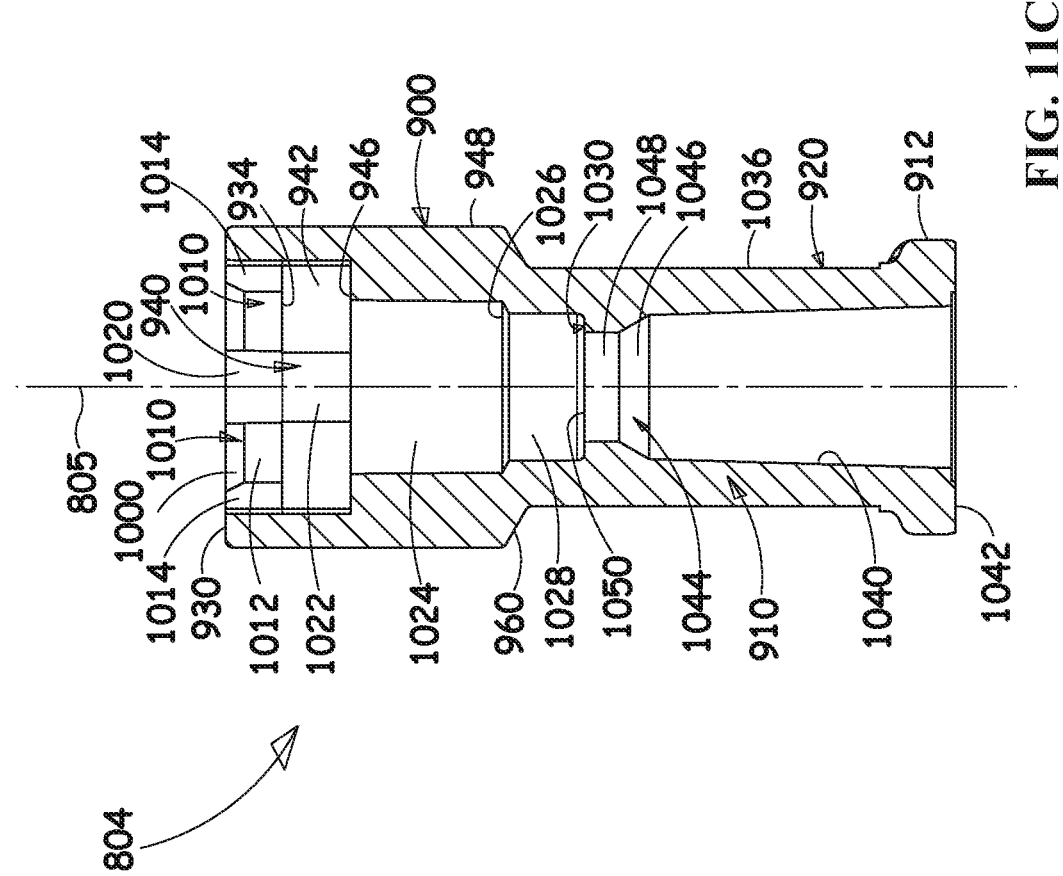

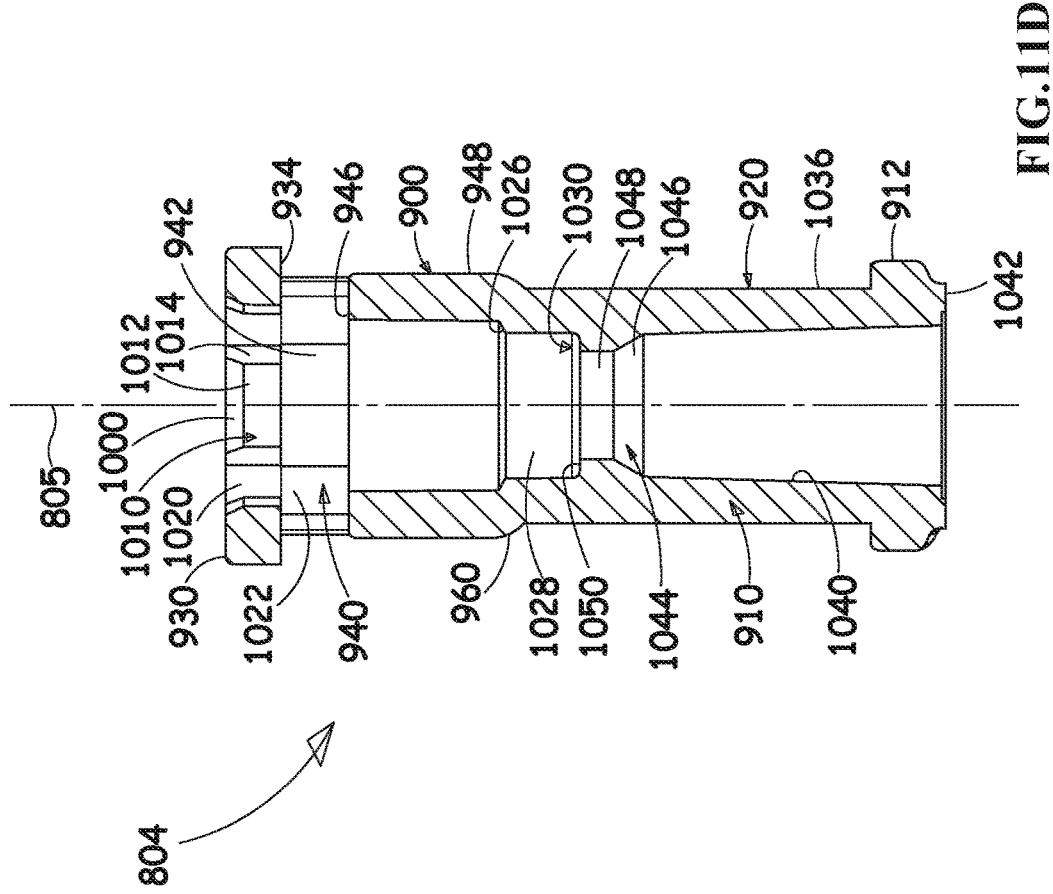

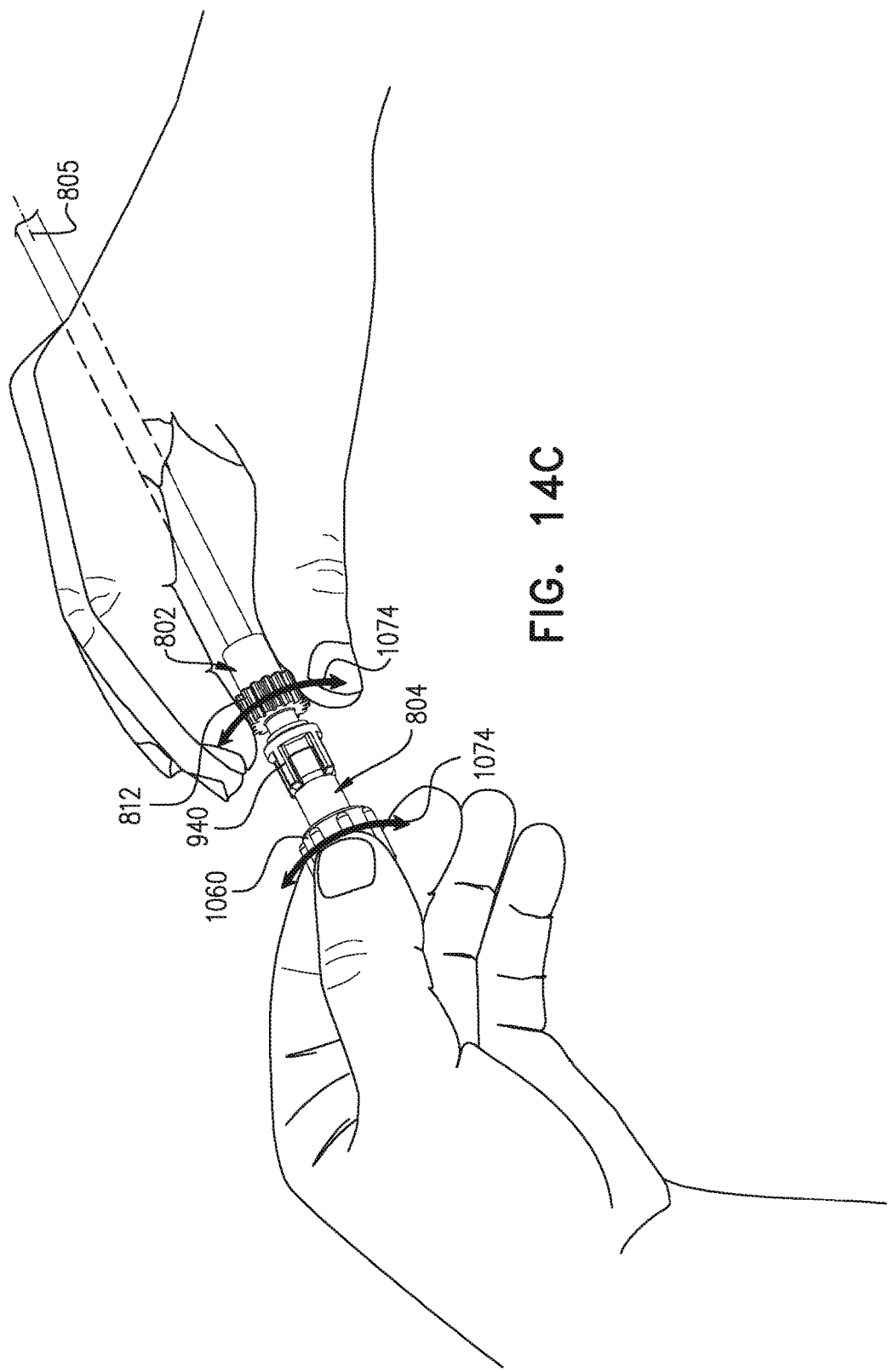

ROTATING CONNECTOR

REFERENCE TO RELATED APPLICATIONS

This application is a National Stage of International Application No. PCT/IL2016/050551 filed May 26, 2016, claiming priority based on U.S. Provisional Patent Application No. 62/167,879 filed May 28, 2015, the contents of all of which are incorporated herein by reference in their entirety.

FIELD OF THE INVENTION

The present invention relates to fluid flow connectors and more particularly to fluid flow connectors for medical applications.

BACKGROUND OF THE INVENTION

Various fluid flow connectors are used for connection of a tube connected to a patient with an IV line or a syringe resulting in a continuous duct for conducting liquids or gases.

SUMMARY OF THE INVENTION

The present invention seeks to provide an improved fluid flow connector.

There is thus provided in accordance with a preferred embodiment of the present invention a rotatable fluid flow connector including a base element and a rotatable element, the rotatable element being non-removably but rotatably connected to the base element for rotation about a common axis.

In accordance with a preferred embodiment of the present invention one of the base element and the rotatable element is formed with a flange having at least one flange surface extending in a plane which is perpendicular to the common axis and another of the base element and the rotatable element is formed with at least one flange engagement surface facing the at least one flange surface and extending in a plane which is perpendicular to the common axis. Additionally or alternatively, the base element is integrally formed with another connector. Alternatively, the base element adapted for a fixed, non-rotatable connection to a tube.

Preferably, the rotating element is integrally formed with a male luer connector. Alternatively, the rotating element is integrally formed with a female luer connector.

In accordance with a preferred embodiment of the present invention the rotating element includes a plurality of elongate portions configured to temporarily bend radially outwardly to provide locking engagement between the rotating element and the base element. Alternatively, the rotating element includes a cylindrical portion configured to temporarily stretch radially outwardly to provide locking engagement between the rotating element and the base element. Additionally, the locking engagement allows rotational movement of the rotating element relative to the base element and limits axial separation between the rotating element and the base element.

There is also provided in accordance with another preferred embodiment of the present invention for use in a rotatable fluid flow connector including a base element, a rotatable element arranged for locking engagement with the base element and rotation with respect thereto about a common axis, the rotatable element being formed with a flange having at least one flange surface extending in a plane which is perpendicular to the common axis.

Preferably, the rotatable element is formed with at least one flange engagement surface extending in a plane which is perpendicular to the common axis and facing at least one flange surface formed on the base element and extending in a plane which is perpendicular to the common axis.

In accordance with a preferred embodiment of the present invention the rotating element is integrally formed with a male luer connector. Alternatively, the rotating element is integrally formed with a female luer connector.

In accordance with a preferred embodiment of the present invention the rotatable element for use in a rotatable fluid flow connector includes a plurality of elongate portions configured to temporarily bend radially outwardly to provide locking engagement between the rotating element and the base element. Alternatively or additionally, the rotatable element for use in a rotatable fluid flow connector also includes a cylindrical portion configured to temporarily stretch radially outwardly to provide locking engagement between the rotating element and the base element. Preferably, the locking engagement allows rotational movement of the rotating element relative to the base element and limits axial separation between the rotating element and the base element.

BRIEF DESCRIPTION OF THE DRAWINGS

The present invention will be understood and appreciated more fully from the following detailed description, taken in conjunction with the drawings in which:

FIGS. 3A, 3B, 3C and 3D are simplified respective pictorial, side view, first end view and second end view illustrations of a rotating element, forming part of the fluid flow connector of FIGS. 1A and 1B;

FIGS. 4A, 4B, 4C, 4D and 4E are, respectively, first and second pictorial sectional illustrations taken along respective lines IVA-IVA and IVB-IVB in FIG. 3A, a partially cut away pictorial sectional illustration taken along lines IVC-IVC in FIG. 3A, and first and second plan view sectional illustrations taken along respective lines IVA-IVA and IVB-IVB in FIG. 3A;

FIGS. 7A, 7B and 7C are simplified pictorial illustrations of three stages of attaching a female luer connector to a rotating element forming part of the fluid flow connector of FIGS. 1A-6C, wherein a base element of the fluid flow connector is connected to a fluid flow conduit;

FIGS. 8A and 8B are simplified pictorial illustrations of a fluid flow connector constructed and operative in accordance with another embodiment of the invention in respective assembled and disassembled operative orientations;

FIGS. 10A, 10B, 10C and 10D are simplified respective pictorial, side view, first end view and second end view illustrations of a rotating element, forming part of the fluid flow connector of FIGS. 8A and 8B;

FIGS. 11A, 11B, 11C and 11D are, respectively, first and second pictorial sectional illustrations taken along respective lines 11A-11A and 11B-11B in FIG. 10A, and first and second plan view sectional illustrations taken along respective lines XIA-XIA and XIB-XIB in FIG. 10A;

FIGS. 14A, 14B and 14C are simplified pictorial illustrations of three stages of attaching a male luer connector to a rotating element forming part of the fluid flow connector of FIGS. 8A-13C, wherein a base element of the fluid flow connector is connected to a fluid flow conduit.

DETAILED DESCRIPTION OF PREFERRED EMBODIMENTS

Figure 1A:
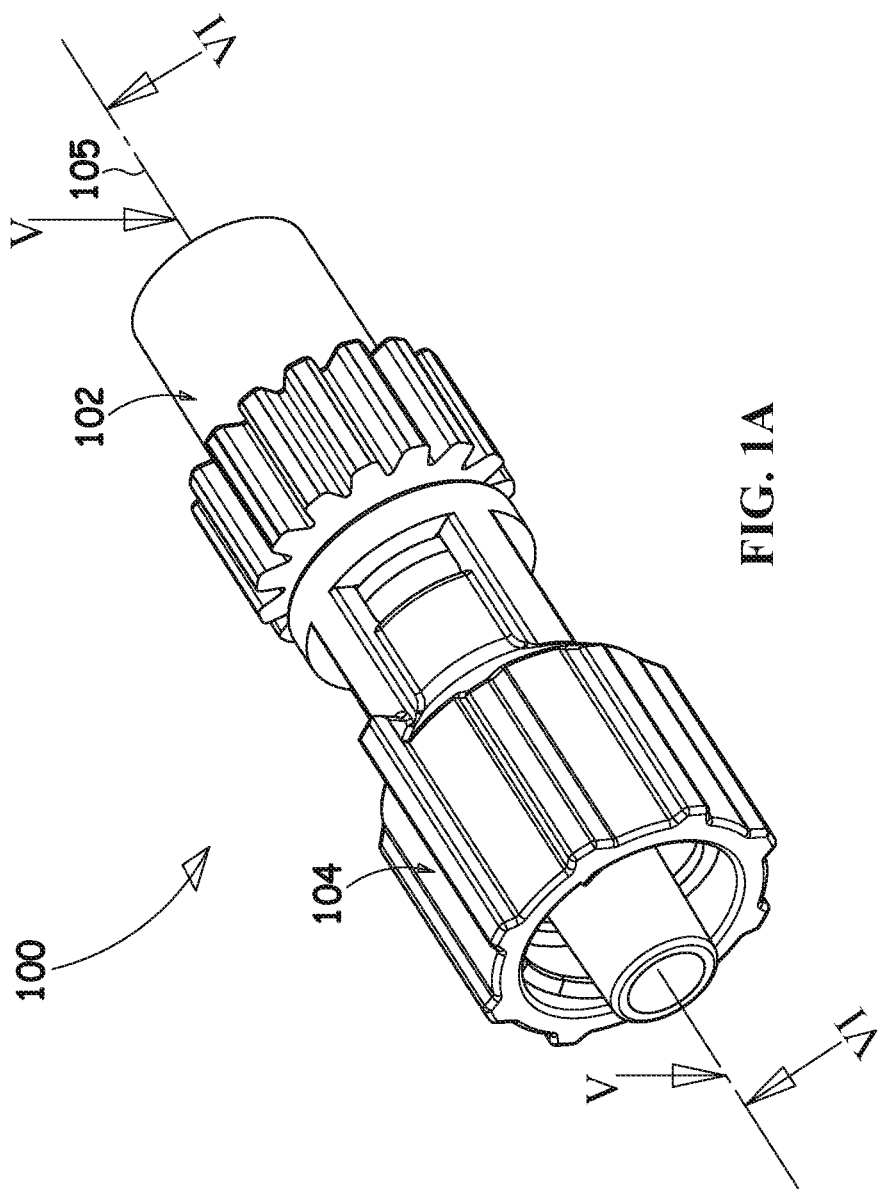
FIGS. 1A and 1B are simplified pictorial illustrations of a fluid flow connector constructed and operative in accordance with an embodiment of the invention in respective assembled and disassembled operative orientations.
Figure 1B:
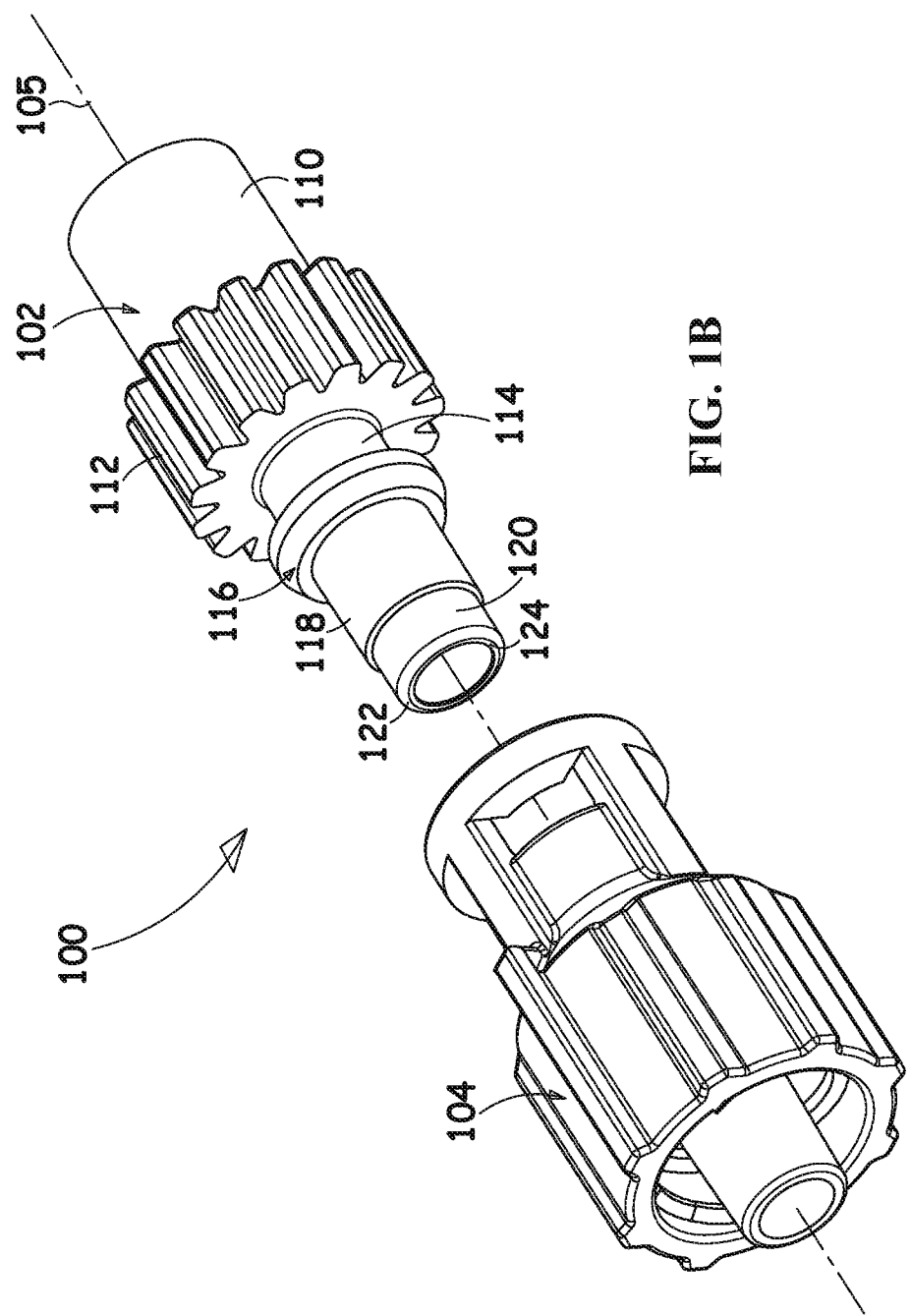

Reference is now made to FIGS. 1A and 1B, which are simplified pictorial illustrations of a fluid flow connector constructed and operative in accordance with an embodiment of the invention in respective assembled and disassembled operative orientations.

As seen in FIGS. 1A and 1B, there is provided a fluid flow connector 100, including a base element 102 and a rotating element 104 which are rotatably and non-removably joined and are arranged along a mutual longitudinal axis 105.

Figure 2A:
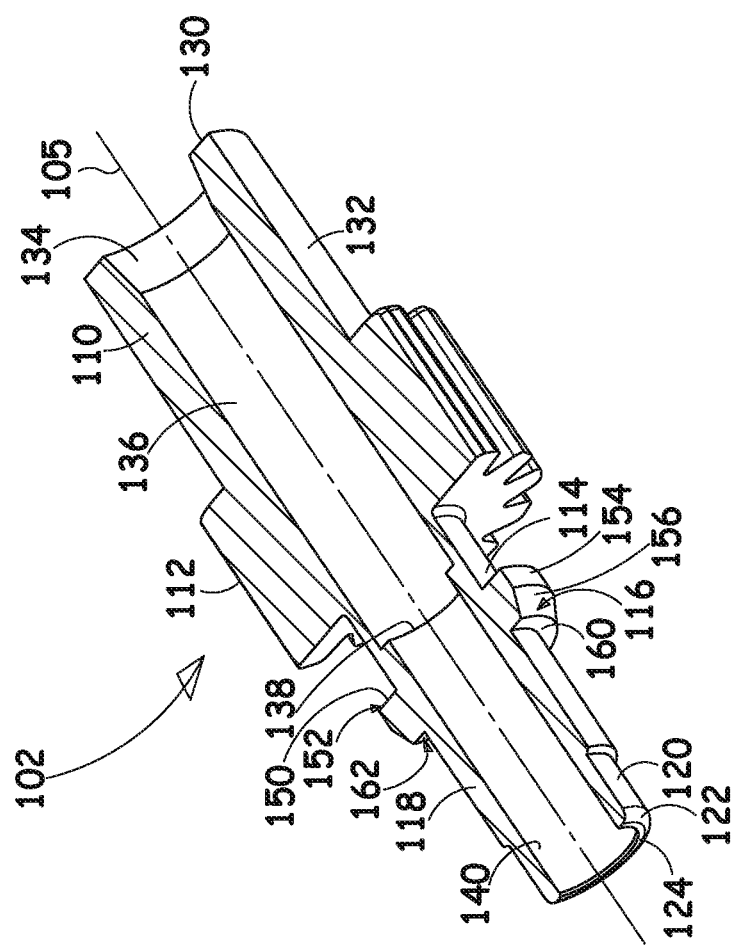
FIGS. 2A and 2B are simplified respective pictorial sectional and plan view sectional illustrations of a base element forming part of the fluid flow connector of FIGS. 1A and 1B.
Figure 2B:
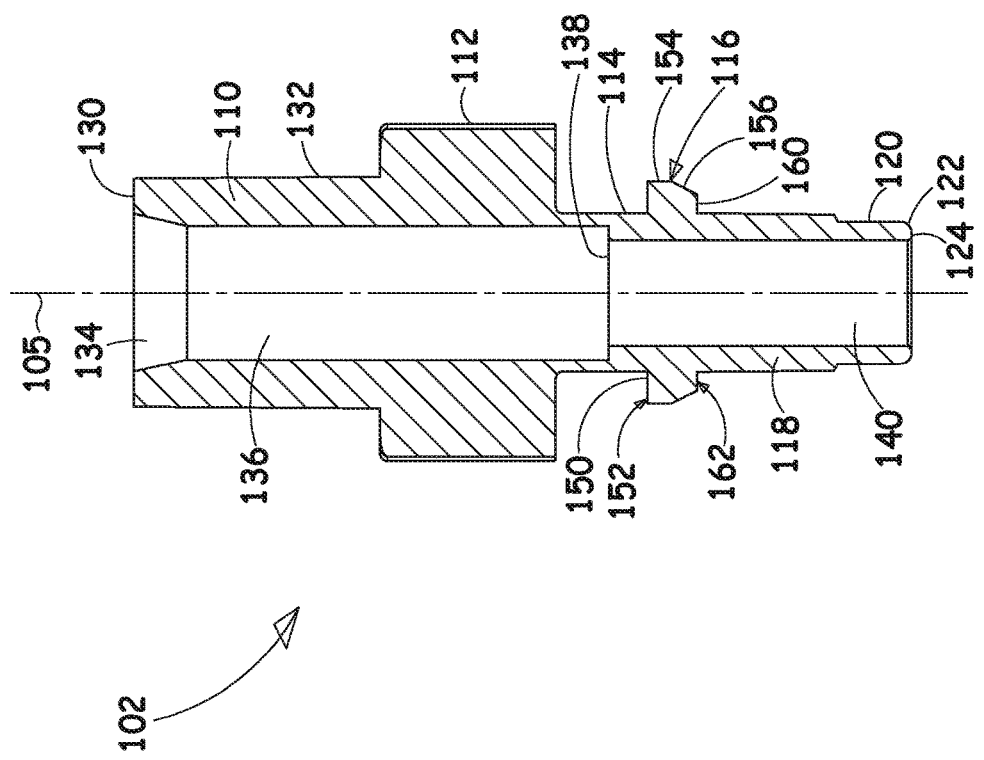

Reference is now additionally made to FIGS. 2A and 2B, which are simplified respective pictorial sectional and plan view sectional illustrations of base element 102.

As seen in FIGS. 1A-2B, base element 102 is preferably an integrally formed element, injection molded of plastic, and includes a generally cylindrical end portion 110, a splined generally cylindrical intermediate portion 112, arranged for being gripped by a user's fingers, a first generally circular cylindrical intermediate portion 114, a flange portion 116, a second generally circular cylindrical intermediate portion 118, a third generally circular cylindrical intermediate portion 120 and a rounded portion 122, terminating in a generally circular ring end surface 124.

As seen particularly in FIGS. 2A and 2B, generally cylindrical end portion 110 includes a generally circular ring end surface 130, which preferably lies in a plane perpendicular to a cylindrical outer surface 132 of generally cylindrical end portion 110. Generally cylindrical end portion 110 preferably includes an inwardly tapered inner surface 134, extending inwardly from generally circular ring end surface 130, and terminating in a first axial circular cylindrical bore 136. First axial circular cylindrical bore 136 extends through splined generally cylindrical intermediate portion 112 and partially into first generally circular cylindrical intermediate portion 114 and terminates at a shoulder 138. A second axial circular cylindrical bore 140, which has a diameter somewhat smaller than that of first axial circular cylindrical bore 136, extends from shoulder 138, through rounded portion 122 to generally circular ring end surface 124.

It is a particular feature of a preferred embodiment of the present invention that flange portion 116 is formed with a generally circular ring surface 150, which preferably lies in a plane perpendicular to first generally circular cylindrical intermediate portion 114 and defines a circumferential 90 degree shoulder 152 with respect thereto.

Flange portion 116 also defines a generally circular cylindrical surface 154, which extends from generally circular ring surface 150 to a generally circular tapered surface 156, which terminates at generally circular ring surface 160, which preferably lies in a plane perpendicular to second generally circular cylindrical intermediate portion 118 and defines a circumferential 90 degree shoulder 162 with respect thereto.

Preferably a tube, such as an IV line, is fixedly connected to base element 102 at first axial circular cylindrical bore 136 and is UV or heat welded thereto.

Figure 3A:
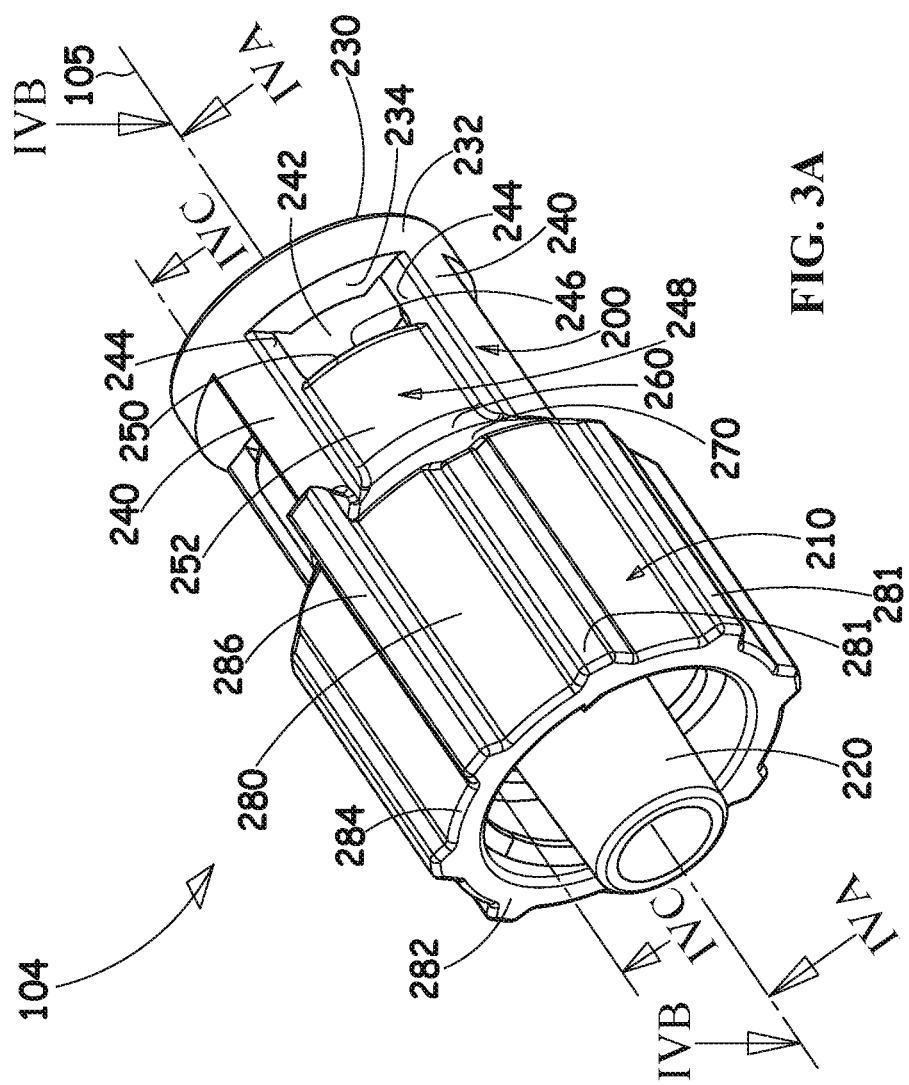
Figure 3B:
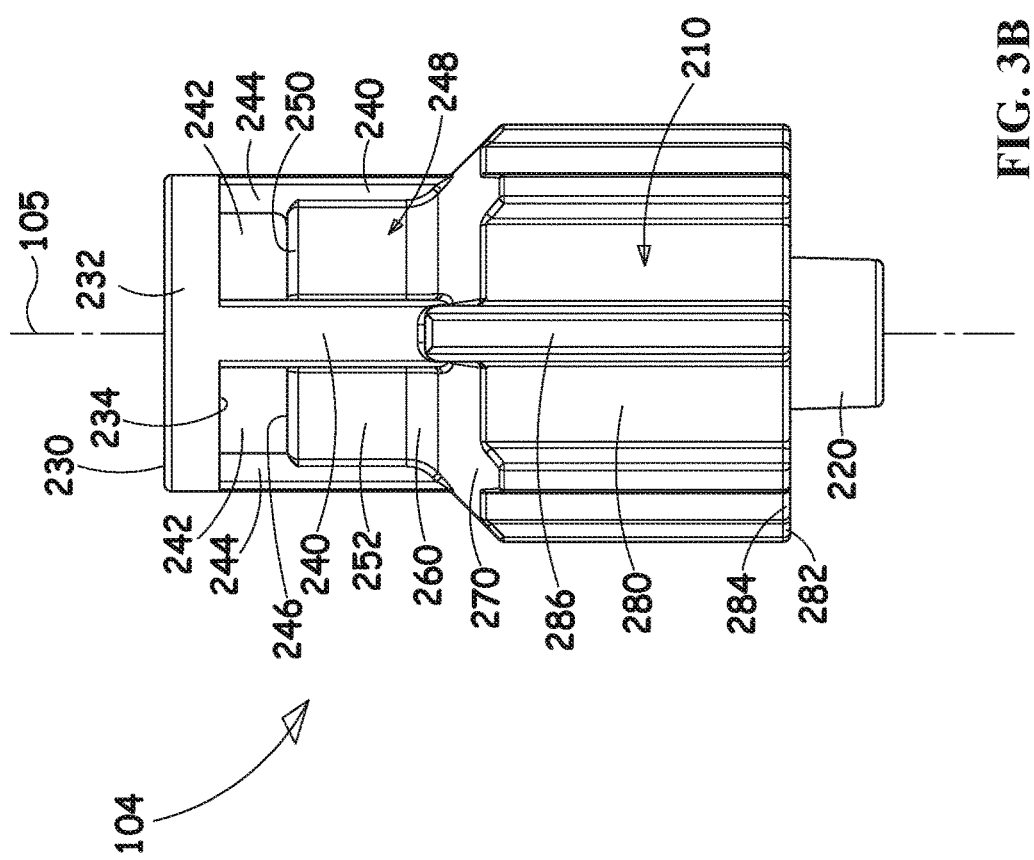
Figure 3C:
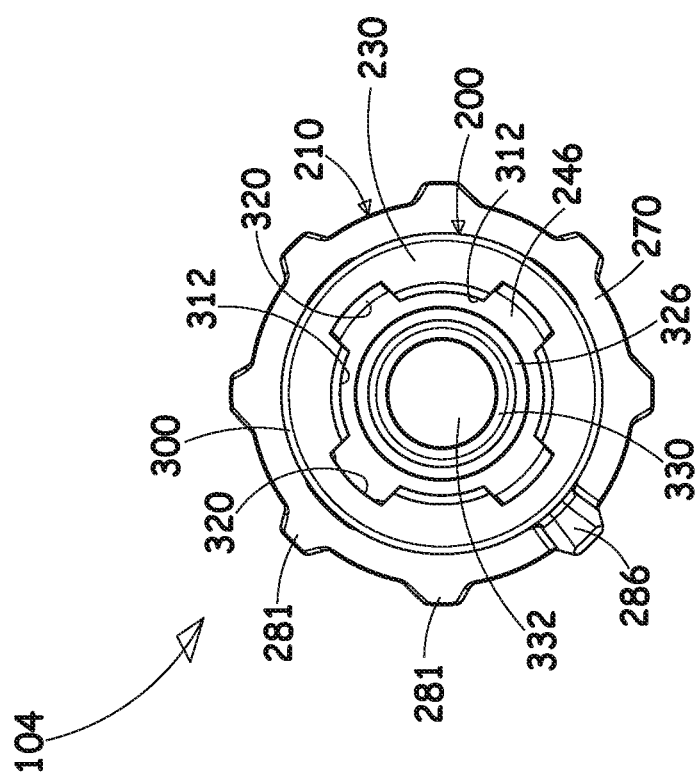
Figure 4B:
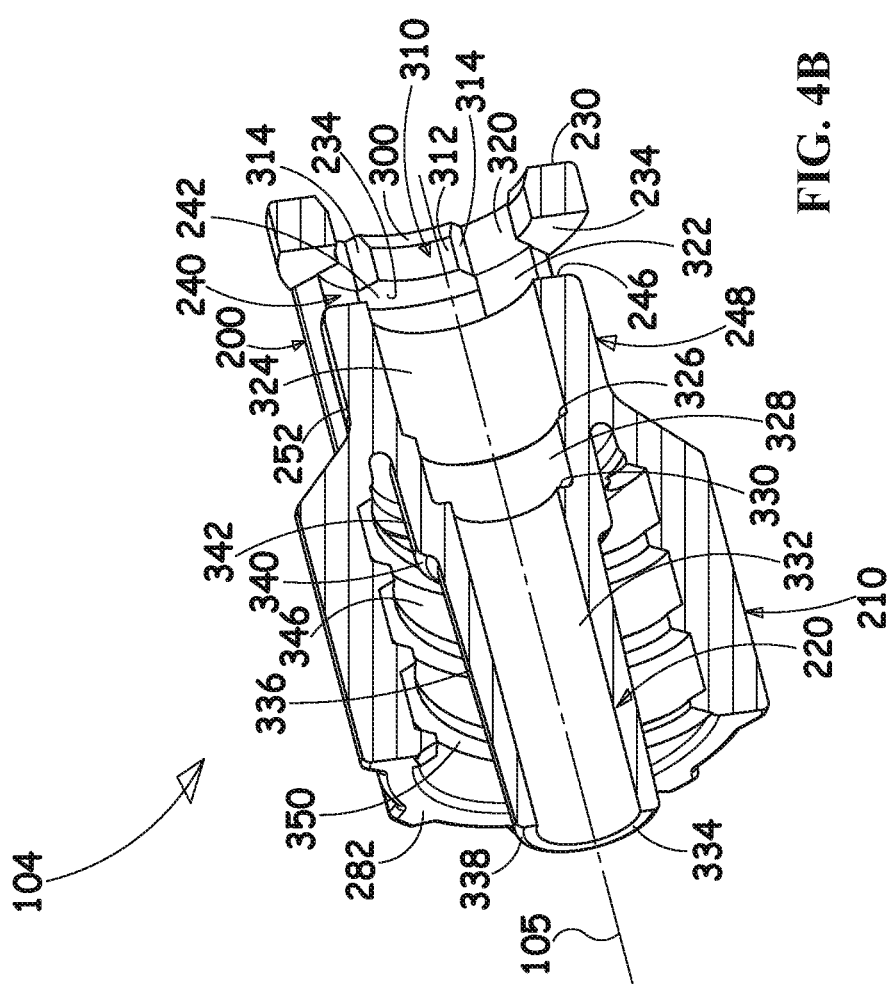
Figure 4C:
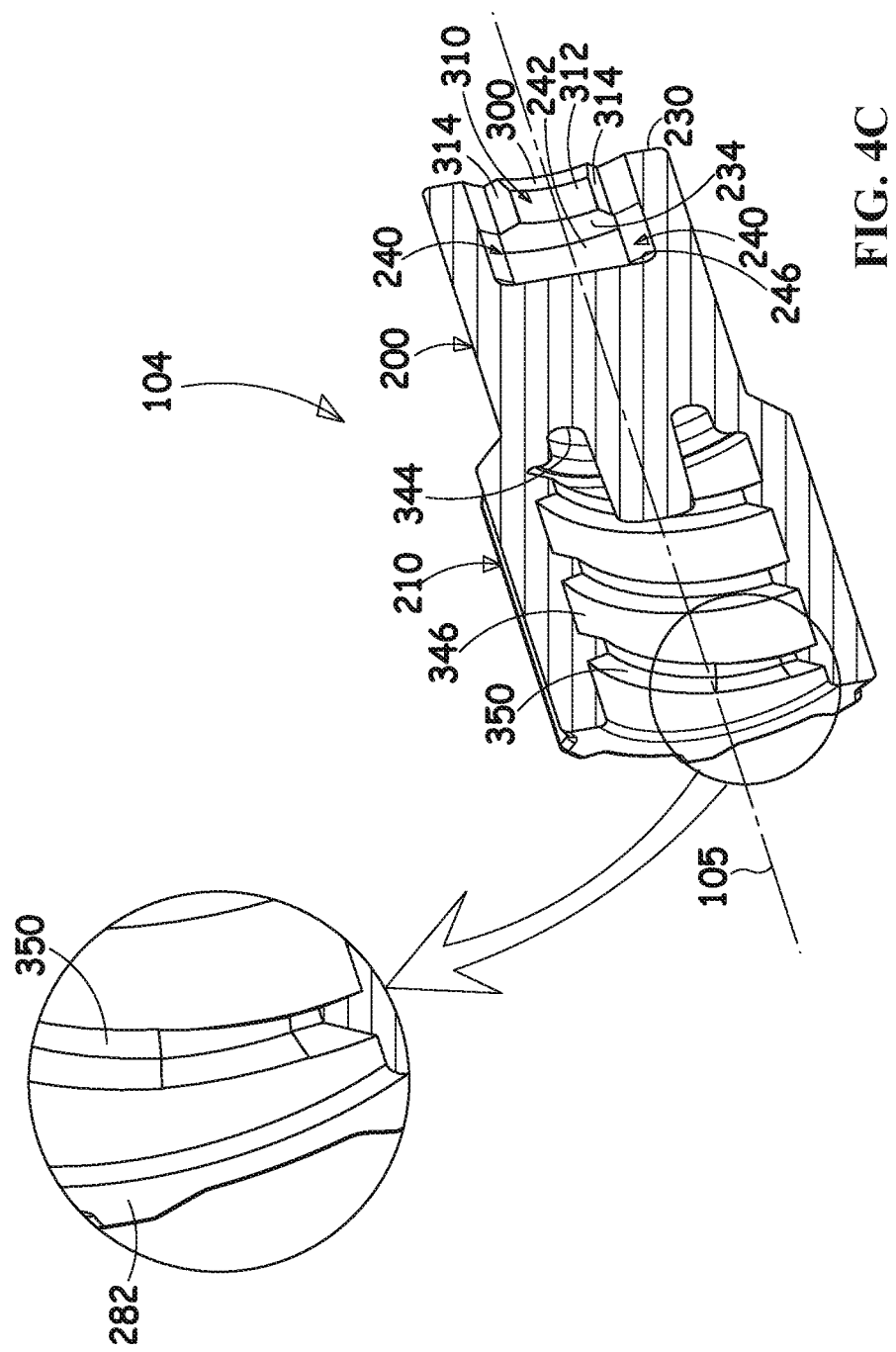
Figure 4D:
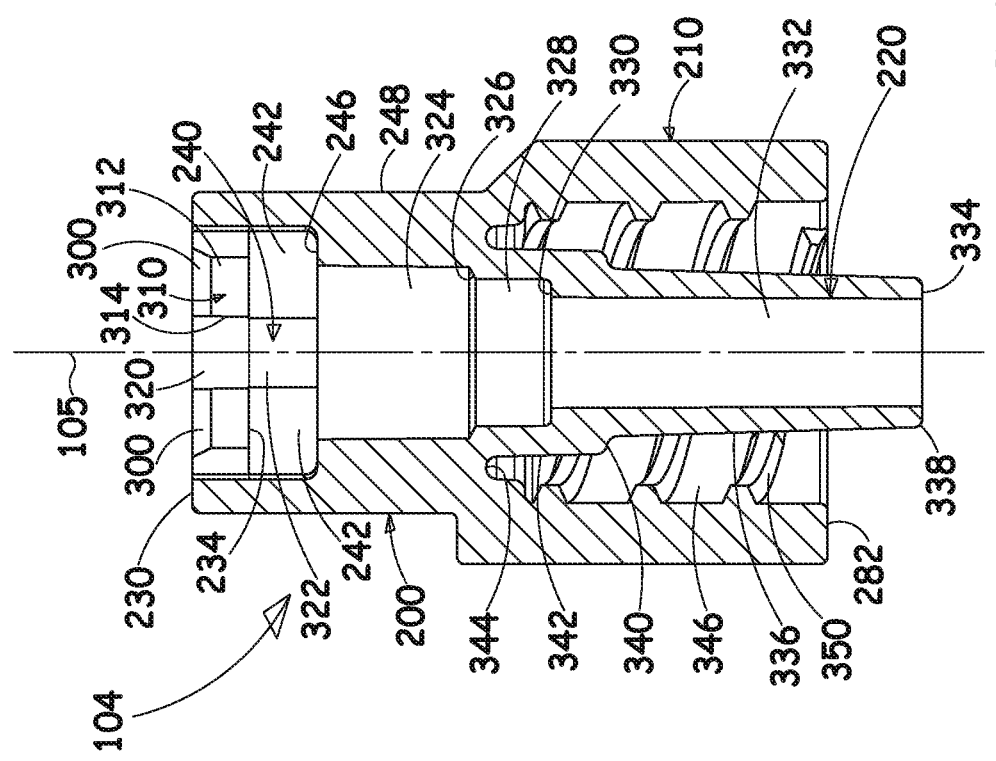

Reference is now made to FIGS. 3A, 3B, 3C and 3D, which are simplified respective pictorial, side view, first end view and second end view illustrations of rotating element 104, forming part of the fluid flow connector of FIGS. 1A and 1B, and to FIGS. 4A, 4B, 4C, 4D and 4E, which are, respectively, first and second pictorial sectional illustrations taken along respective lines IVA-IVA and IVB-IVB in FIG. 3A, a partially cut away pictorial sectional illustration taken along lines IVC-IVC in FIG. 3A, and first and second plan view sectional illustrations taken along respective lines IVA-IVA and IVB-IVB in FIG. 3A.

As seen particularly in FIGS. 3A-3D, rotating element 104 is preferably an integrally formed generally circularly symmetric element arranged about longitudinal axis 105. Rotating element 104 is preferably injection molded of plastic and includes a first generally cylindrical portion 200 and a second generally cylindrical portion 210, having an overall outer diameter which is greater than that of first generally cylindrical portion 200. A male luer connector portion 220 extends through most of second generally cylindrical portion 210 and therebeyond.

First generally cylindrical portion 200 preferably includes a generally circular ring end surface 230 from which extends, about longitudinal axis 105 a generally circular cylindrical surface 232. It is a particular feature of an embodiment of the present invention that generally circular cylindrical surface 232 terminates at a generally circular broken ring surface 234, which is preferably parallel to generally circular ring end surface 230 and lies in a plane perpendicular to axis 105 and to generally circular cylindrical surface 232.

A plurality of mutually separated elongate portions 240, preferably four in number, extend from generally circular broken ring surface 234 towards second generally cylindrical portion 210 and define therebetween a plurality of windows 242, preferably four in number. Windows 242 are preferably each bounded by a portion of generally circular broken ring surface 234, by a pair of radially extending side surfaces 244 of adjacent elongate portions 240 and by a generally circular ring end surface 246 of a generally cylindrical portion 248. Generally circular ring end surface 246 preferably lies in a plane parallel to that of generally circular broken ring surface 234 and preferably defines a rounded circumferential corner edge 250 with a generally circular cylindrical outer surface 252 of generally cylindrical portion 248.

Generally circular cylindrical outer surface 252 extends from generally circular ring end surface 246 to a tapered generally circumferential surface 260, which extends, in turn, to a generally tapered generally circumferential outer surface 270 of second generally cylindrical portion 210.

Generally tapered generally circumferential outer surface 270 extends to a generally cylindrical outer splined surface 280 of second generally cylindrical portion 210, which defines a plurality of ribs 281 and terminates at a generally circularly symmetric ring end surface 282 and defines a chamfered circumferential edge 284 therewith. It is noted that one of the plurality of ribs 281, here designated by reference numeral 286, extends over part of the first generally cylindrical portion 200.

Referring now specifically to FIGS. 4A, 4B, 4C, 4D and 4E, it is seen that generally circular ring end surface 230 terminates radially inwardly in a plurality of tapered circumferential surfaces 300, each formed on a radially inward edge of a corresponding window lintel portion 310, extending between adjacent elongate portions 240. Each window lintel portion 310 also includes a generally circular cylindrical radially inward facing surface portion 312 and a pair of radially extending side wall portions 314, all of which terminate at generally circular broken ring surface 234.

It is a particular feature of an embodiment of the present invention that the junction between radially inward facing surface portion 312 and generally circular broken ring surface 234 defines a mutually perpendicular, generally circumferential shoulder 313.

It is also seen that azimuthally intermediate window lintel portions 310 there are defined generally circular cylindrical inwardly facing surface portions 320, which extend into corresponding generally circular cylindrical inwardly facing surface portions 322, which terminate at ring surface 246.

A first generally circularly symmetric inner facing bore surface 324 extends through generally cylindrical portion 248 to a shoulder 326, preferably 90 degrees, from which extends a second generally circularly symmetric inner facing bore surface 328. Second generally circularly symmetric inner facing bore surface 328 extends to a shoulder 330, preferably 90 degrees, from which extends a third generally circularly symmetric inner facing bore surface 332. Third generally circularly symmetric inner facing bore surface 332 extends through male luer connector 220 to a generally circular luer connector end ring surface 334.

Male luer connector 220 defines a tapered outer surface 336 which extends from generally circular luer connector end ring surface 334 at a rounded circumferential edge 338 to a tapered shoulder 340 from which extends a generally cylindrical surface 342. Generally cylindrical surface 342 terminates in a circumferential recess 344 having a partially circular cross section. Extending from circumferential recess 344 on an inner facing surface 346 spaced from tapered outer surface 336 of male luer connector 220 is a luer threading 350. It is a particular feature of the luer threading 350 that its pitch increases as it progresses from a location adjacent circumferential recess 344 to a location adjacent generally circularly symmetric ring end surface 282.

Figure 5A:
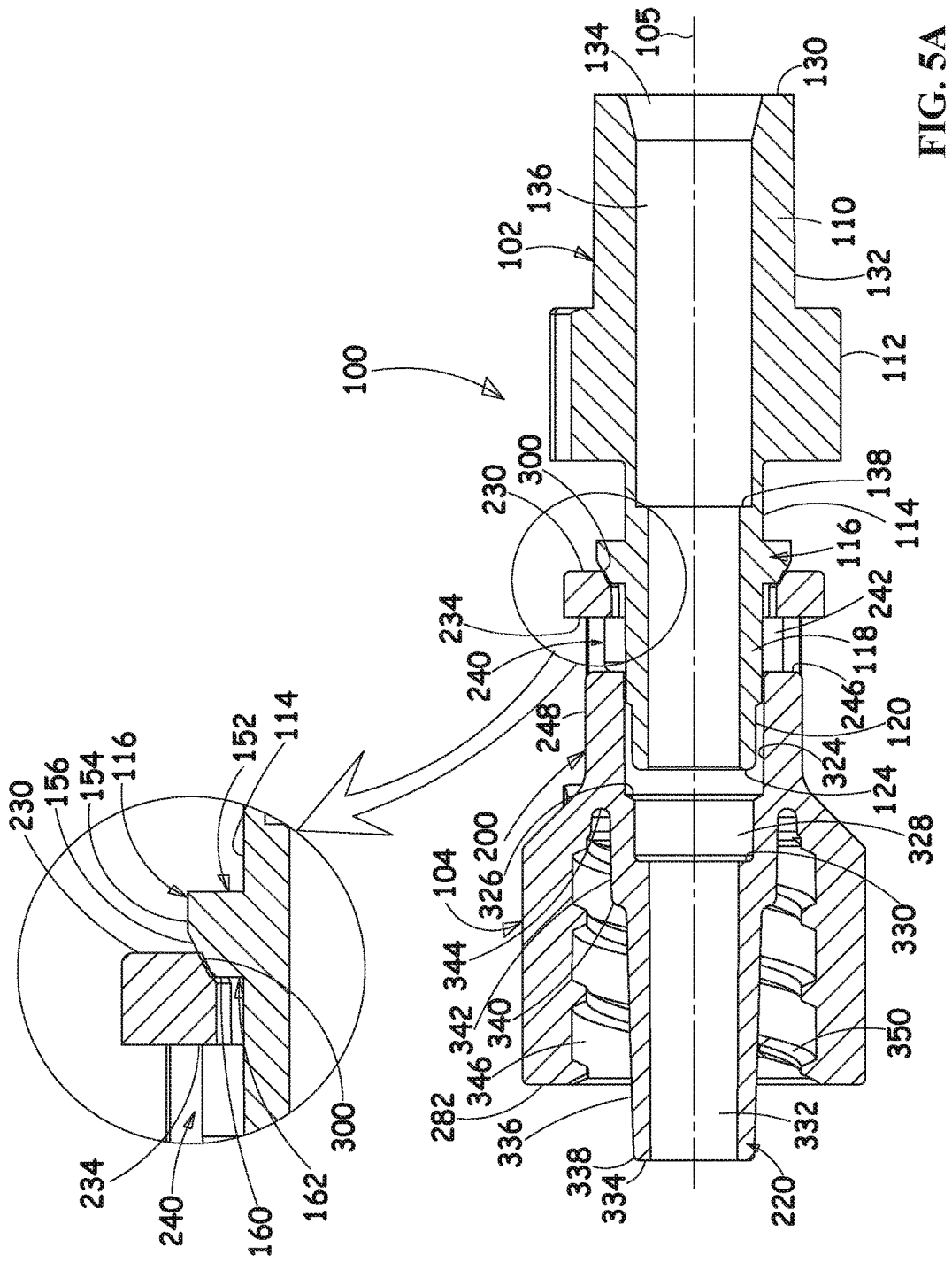
FIGS. 5A, 5B and 5C are simplified plan view sectional illustrations taken along lines V-V in FIG. 1A, which illustrate three stages in the assembly of the fluid flow connector of FIGS. 1A-4E.
Figure 5B:
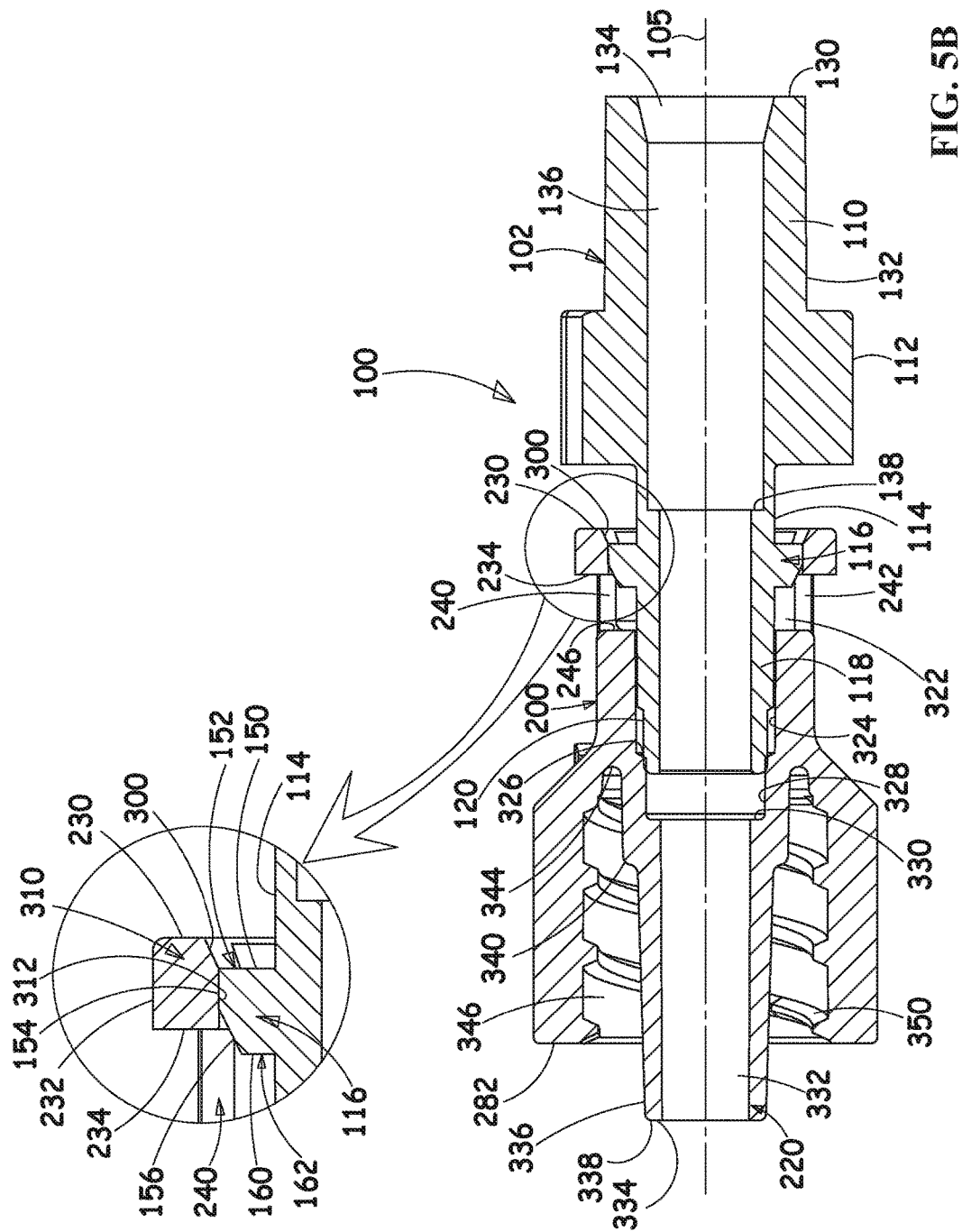
Figure 5C:
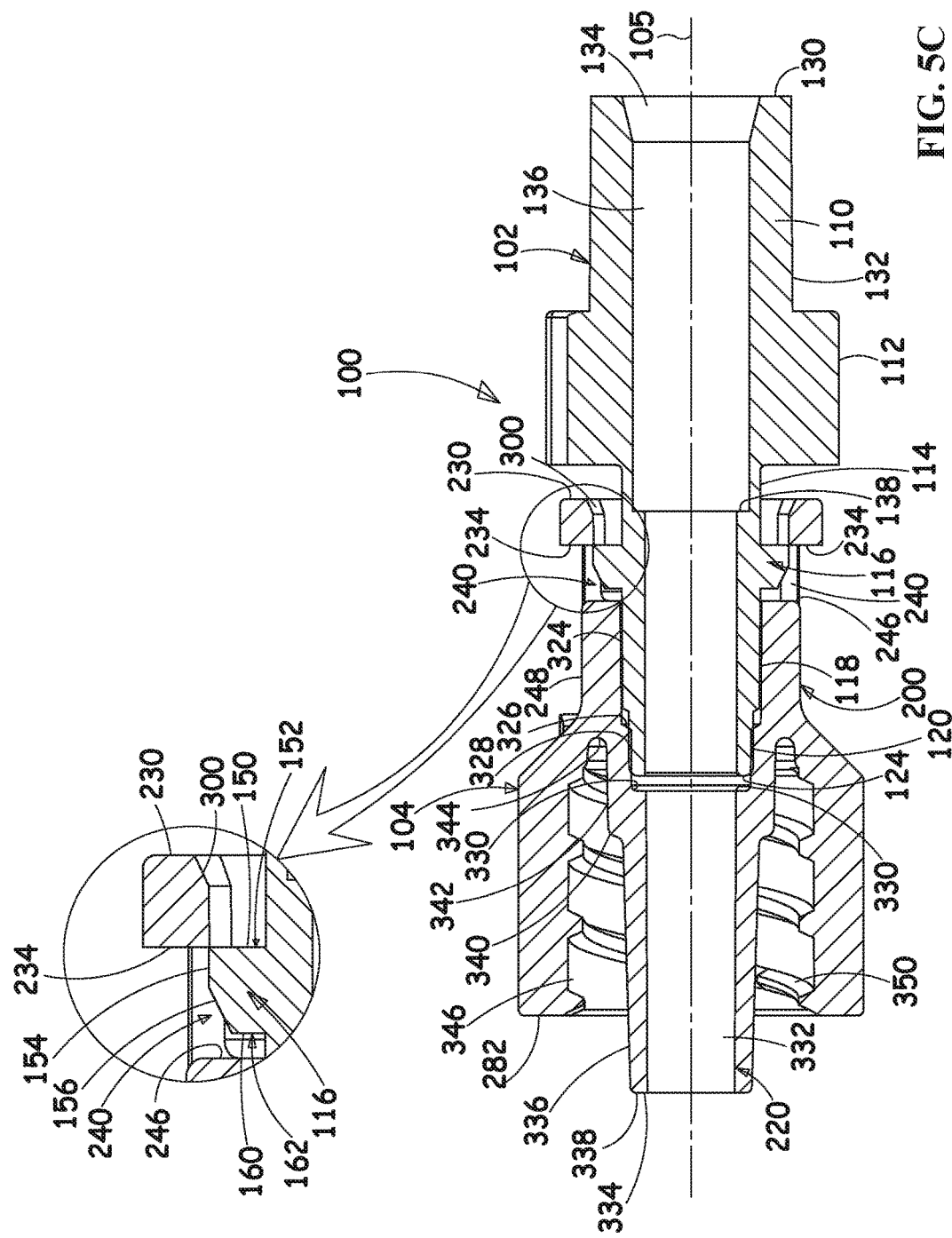
Figure 6A:
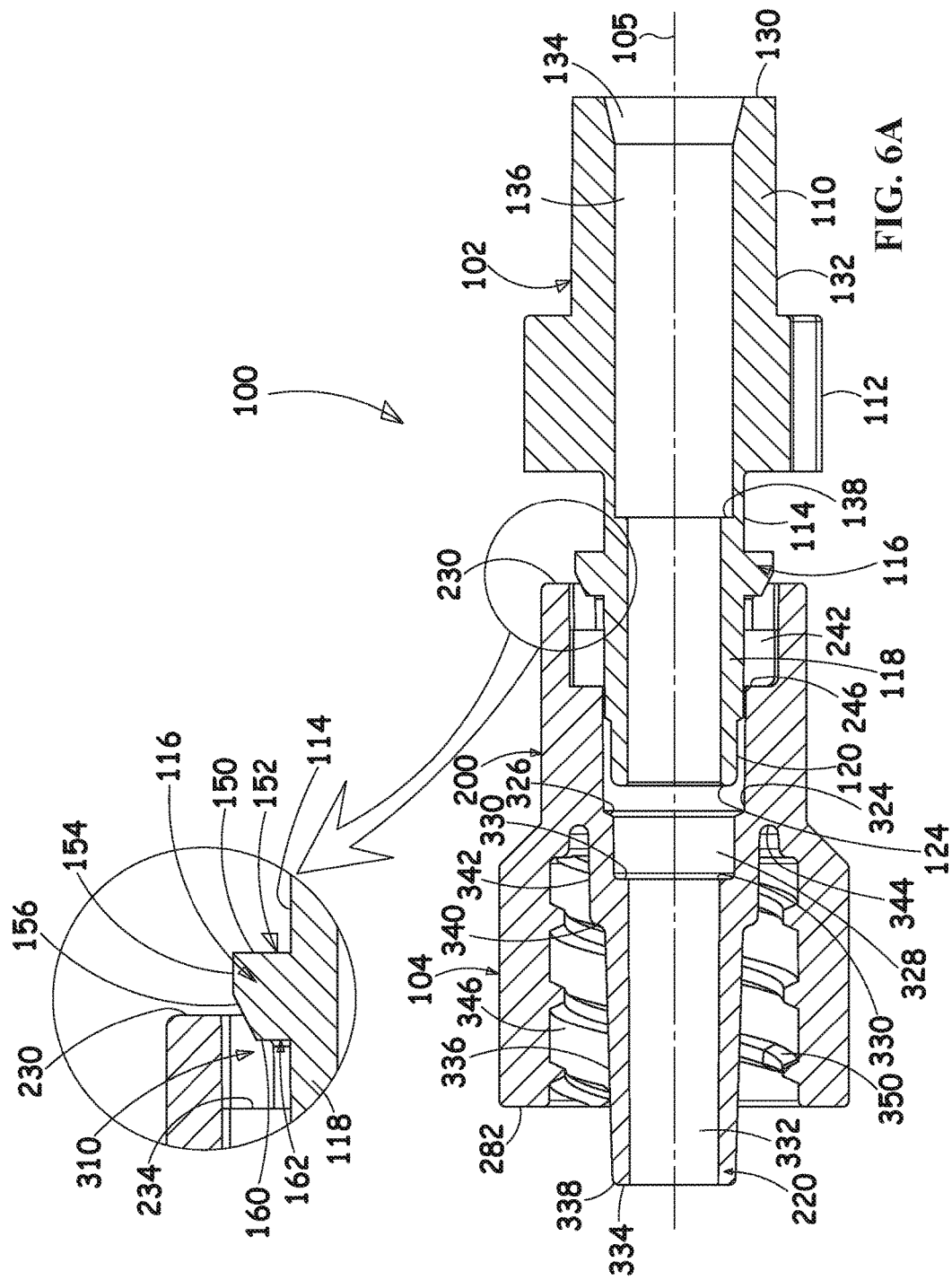
FIGS. 6A, 6B and 6C are simplified plan view sectional illustrations taken along lines VI-VI in FIG. 1A, which illustrate three stages in the assembly of the fluid flow connector of FIGS. 1A-4E.
Figure 6B:
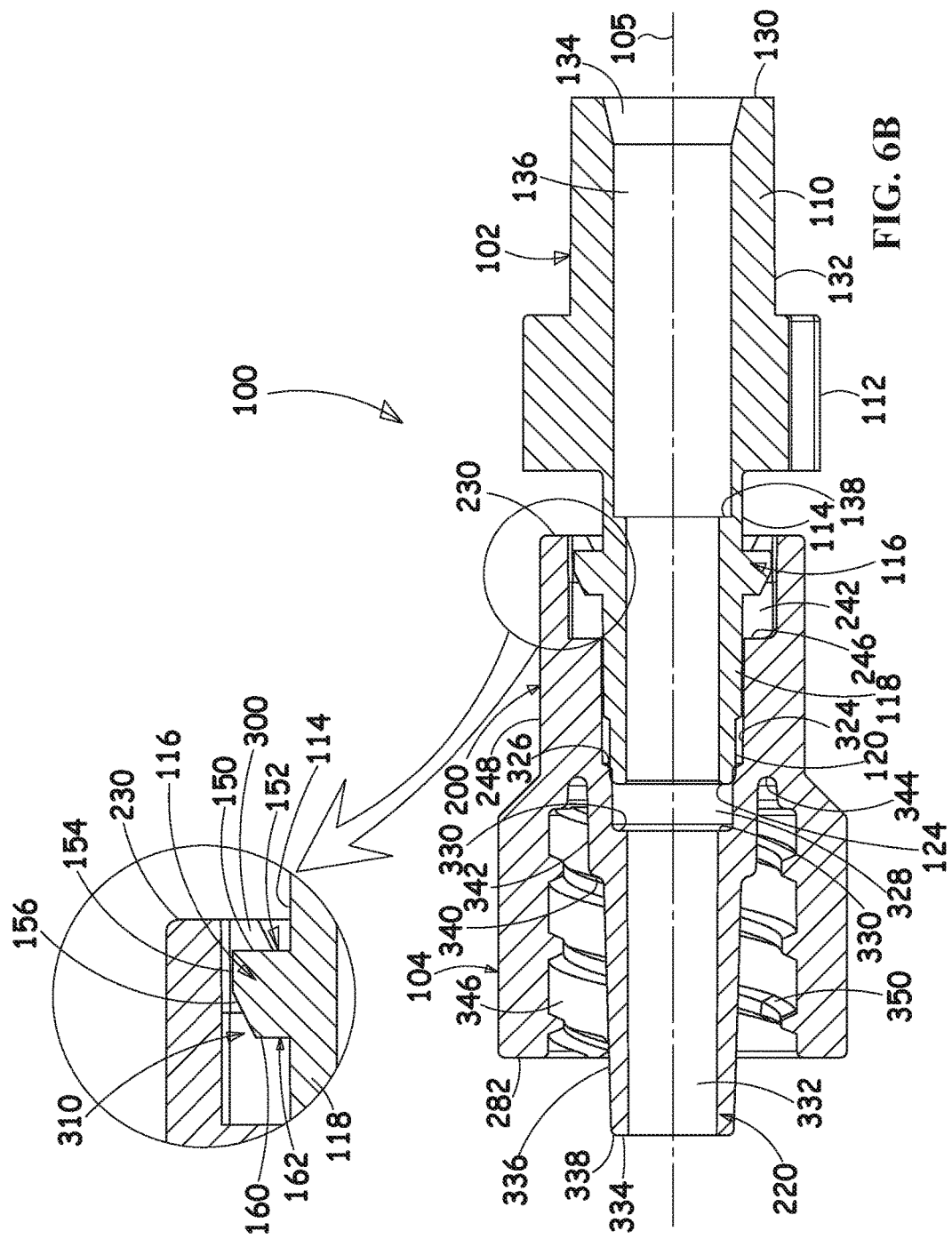
Figure 6C:
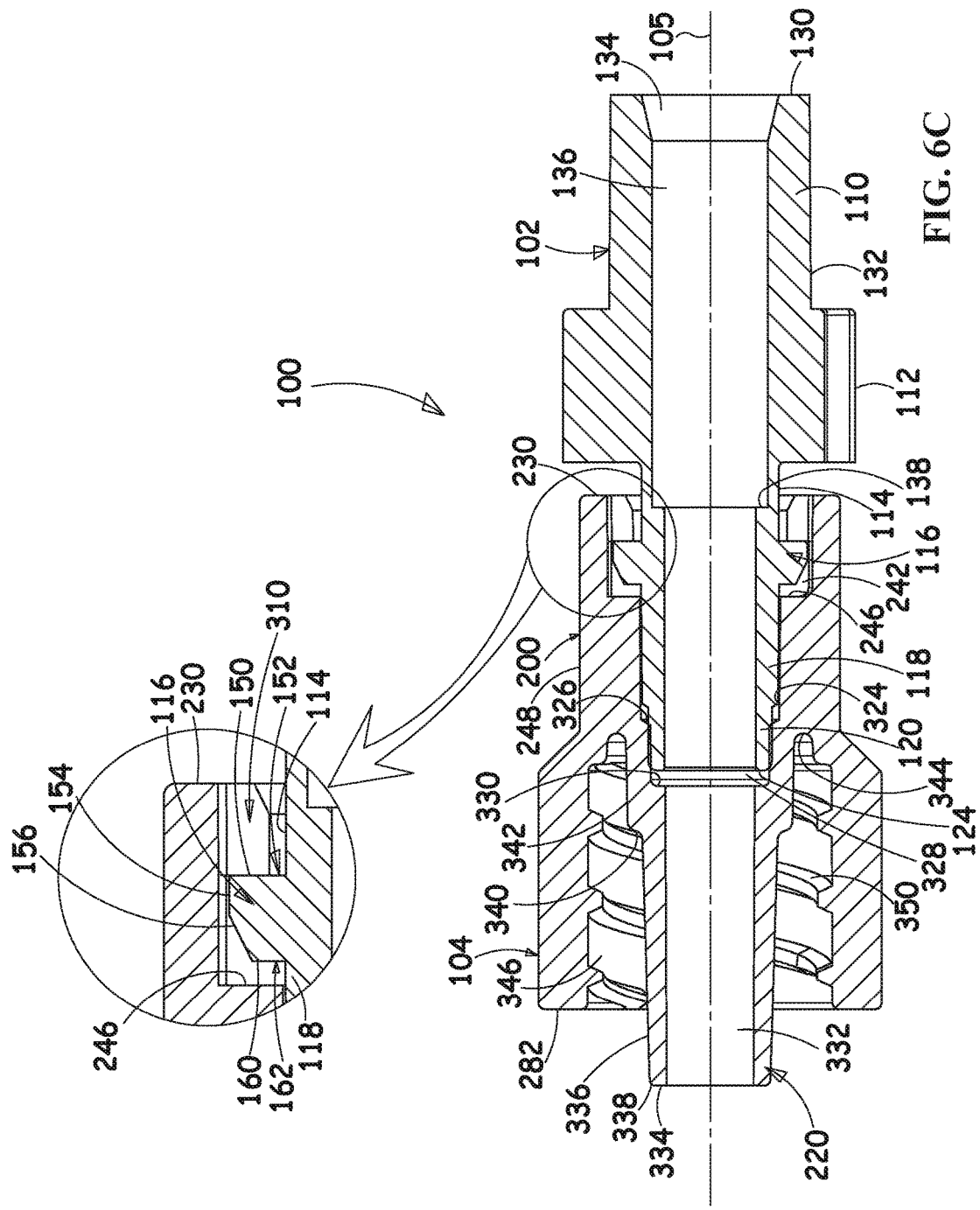

Reference is now made to FIGS. 5A, 5B and 5C are simplified plan view sectional illustrations taken along lines V-V in FIG. 1A, and to FIGS. 6A, 6B and 6C, which are simplified plan view sectional illustrations taken along lines VI-VI. FIGS. 5A-5C and FIGS. 6A-6C each illustrate the same three stages in the assembly of the fluid flow connector 100 of FIGS. 1A-4E.

Turning initially to FIGS. 5A and 6A, and particularly to FIG. 5A, it is seen that both base element 102 and rotating element 104 are arranged along mutual longitudinal axis 105. Tapered circumferential surfaces 300 of rotating element 104 engage circular tapered surface 156 of flange portion 116 of base element 102. Second generally circular cylindrical intermediate portion 118 of base element 102 engages circularly symmetric inner facing bore surface 324 of rotating element 104.

Turning now to FIGS. 5B and 6B, and particularly to FIG. 5B, it is seen that generally circular cylindrical radially inward facing surface portions 312 of rotating element 104 engage generally circular cylindrical surface 154 of flange portion 116 of base element 102, thereby temporarily bending elongate portions 240 radially outwardly and temporarily stretching first generally cylindrical portion 200 at generally circular ring end surface 230 and circular cylindrical surface 232. Third generally circular cylindrical intermediate portion 120 of base element 102 engages second generally circularly symmetric inner facing bore surface 328 of rotating element 104.

FIGS. 5C and 6C, and particularly FIG. 5C, illustrate mutually rotatable, mutually axially locked engagement of rotating element 104 with base element 102, which is a particular feature of an embodiment of the present invention. It is seen that generally circular broken ring surface 234 of rotating element 104 rotatably engages generally circular ring surface 150 of base element 102 at shoulder 152, thereby locking rotating element 104 and base element 102 against mutual axial separation along axis 105. It is also seen that third generally circular cylindrical intermediate portion 120 of base element 102 engages second generally circularly symmetric inner facing bore surface 328 of rotating element 104 at shoulder 330, thereby limiting the axial distance along which rotating element 104 and base element 102 can approach each other along axis 105. It is also seen that elongate portions 240 are no longer bent radially outwardly and that first generally cylindrical portion 200 is no longer stretched at generally circular ring end surface 230 and circular cylindrical surface 232.

Figure 7A:
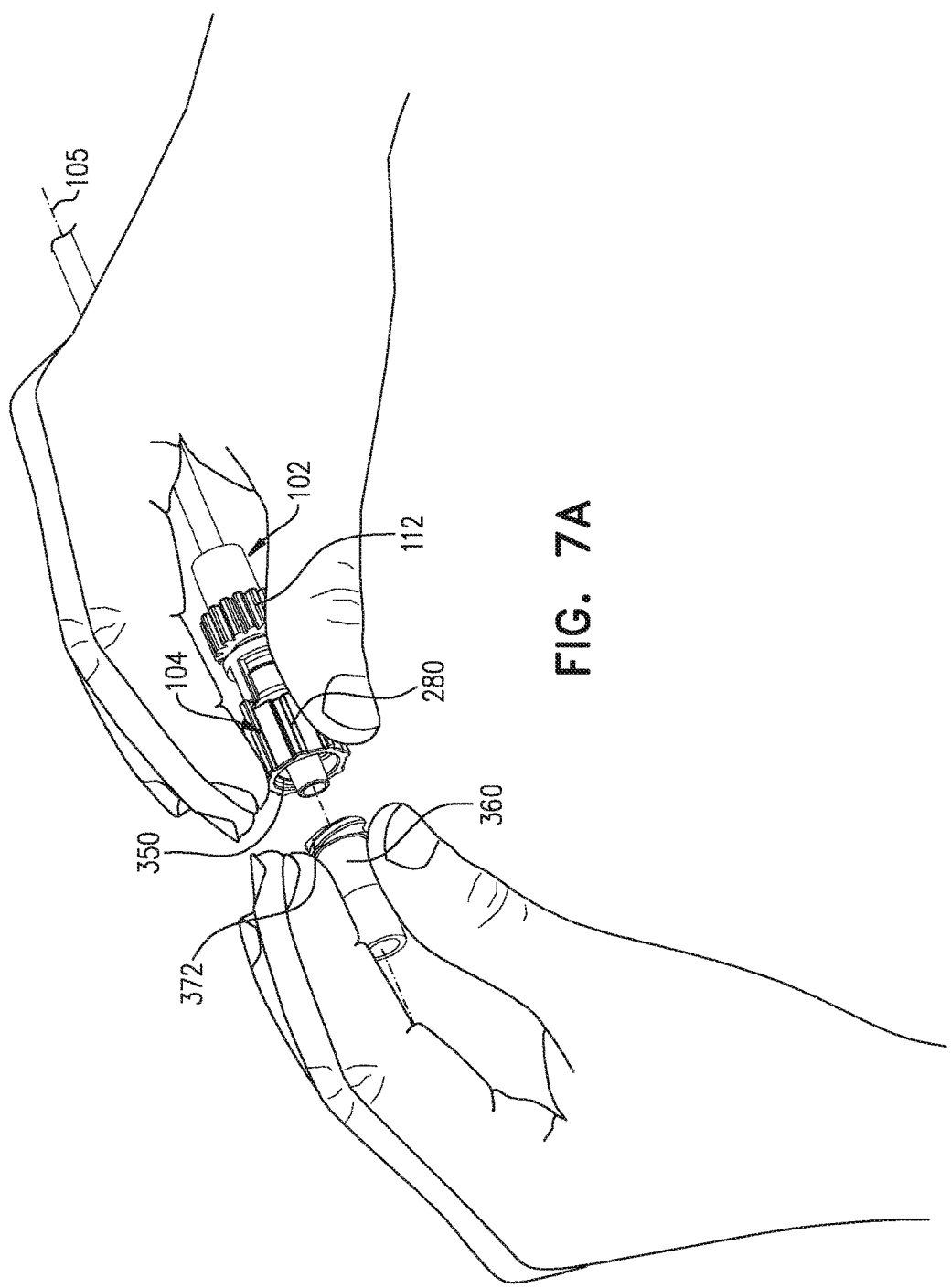

Reference is now made to FIGS. 7A, 7B and 7C, which are simplified pictorial illustrations of three stages of attaching a female luer connector to a rotating element forming part of the fluid flow connector of FIGS. 1A-6C, wherein a base element of the fluid flow connector is connected to a fluid flow conduit.

Turning initially to FIG. 7A, it is seen that a user holds rotating element 104, typically in the user's right hand, typically gripping it at ribs 281 of generally cylindrical outer splined surface 280 of second generally cylindrical portion 210, and holds a female luer connector 360, typically in the user's left hand, mutually orienting the luer connector 360 along longitudinal axis 105 of the joined base element 102 and rotating element 104.

Turning now to FIG. 7B, it is seen that the user, typically using the user's right hand, rotates the rotating element 104 in a direction indicated by an arrow 370 by gripping ribs 281 of generally cylindrical outer splined surface 280 of second generally cylindrical portion 210, thus threadably engaging an outwardly threaded surface 372 of luer connector 360 with luer threading 350 of rotating element 104.

Turning now to FIG. 7C, it is seen that following threaded engagement of outwardly threaded surface 372 of luer connector 360 with luer threading 350 of rotating element 104, the rotating element 104 may be freely rotated relative to the base element 102. This is illustrated by showing that the user holds base element 102, typically in the user's right hand, gripping it at splined generally cylindrical intermediate portion 112, while typically the user's left hand rotates the rotating element 104, as indicated by an arrow 374.

Figure 8A:
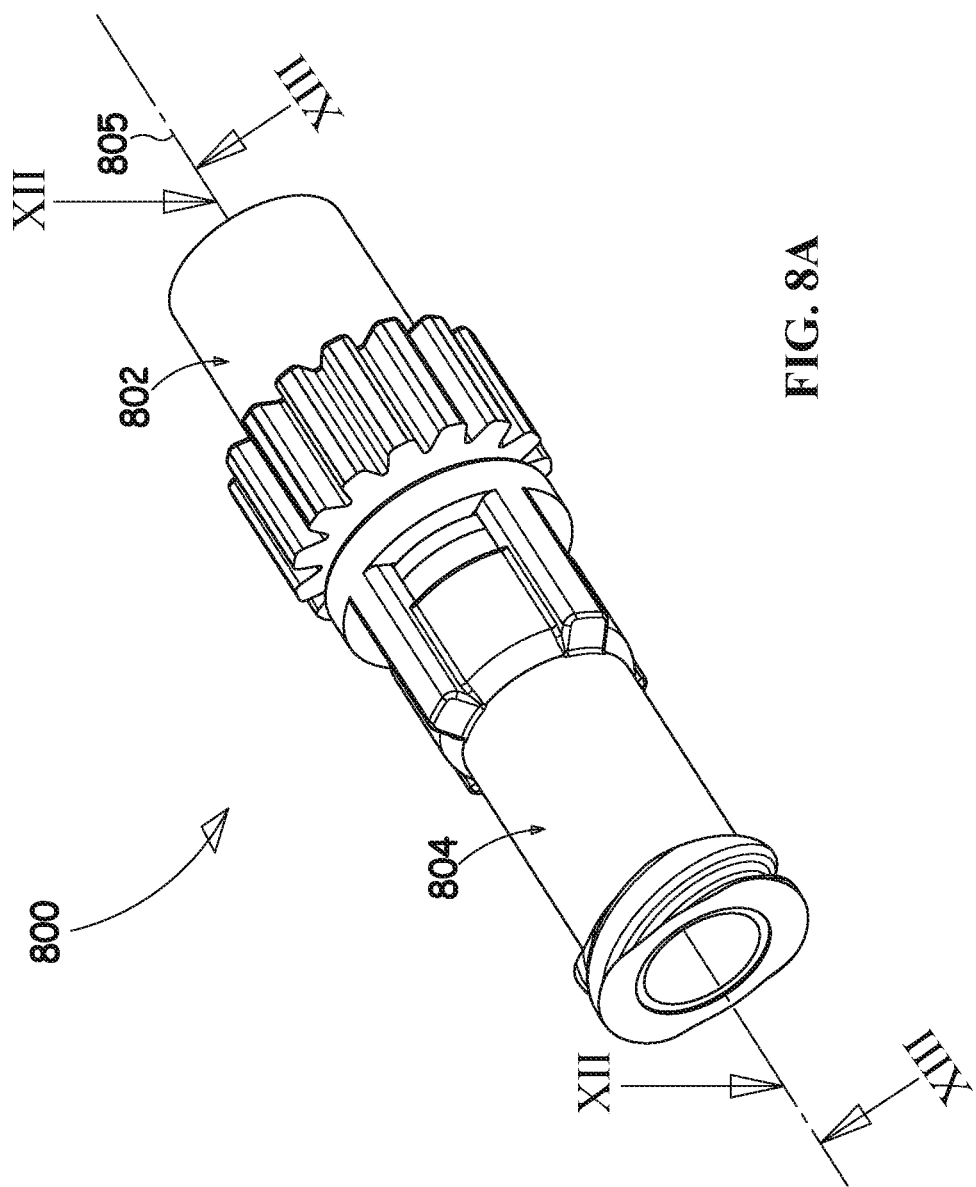

Reference is now made to FIGS. 8A and 8B, which are simplified pictorial illustrations of a fluid flow connector constructed and operative in accordance with an embodiment of the invention in respective assembled and disassembled operative orientations.

As seen in FIGS. 8A and 8B, there is provided a fluid flow connector 800, which includes a base element 802 and a rotating element 804, which are rotatably and non-removably joined and are arranged along a mutual longitudinal axis 805.

Figure 9A:
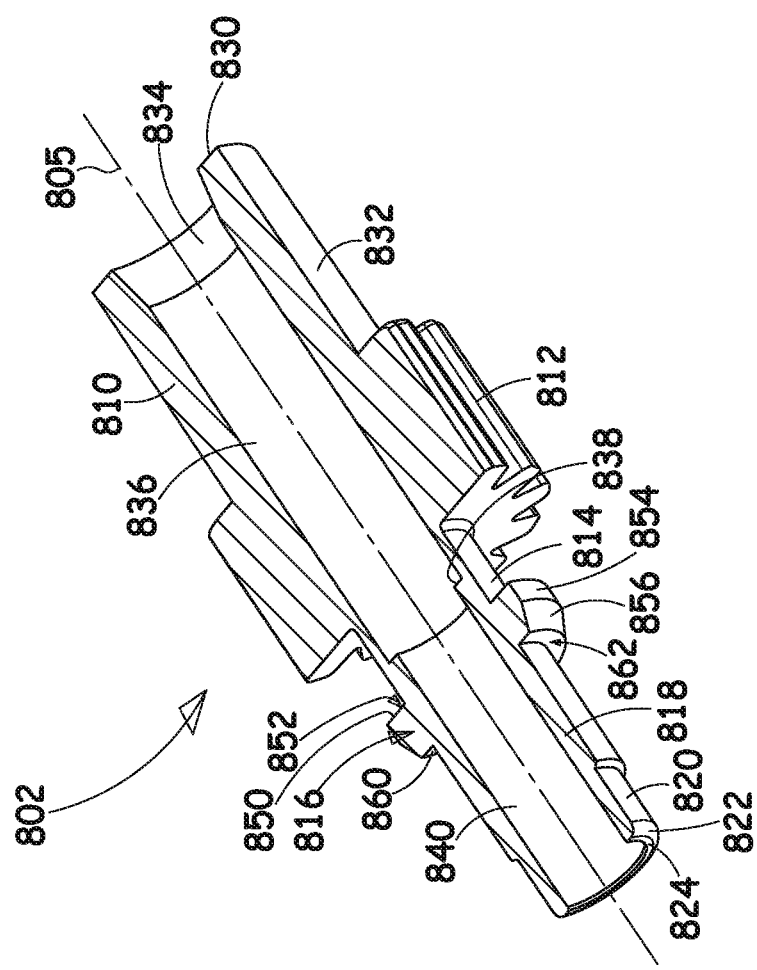
FIGS. 9A and 9B are simplified respective pictorial sectional and plan view sectional illustrations of a base element forming part of the fluid flow connector of FIGS. 8A and 8B.
Figure 9B:
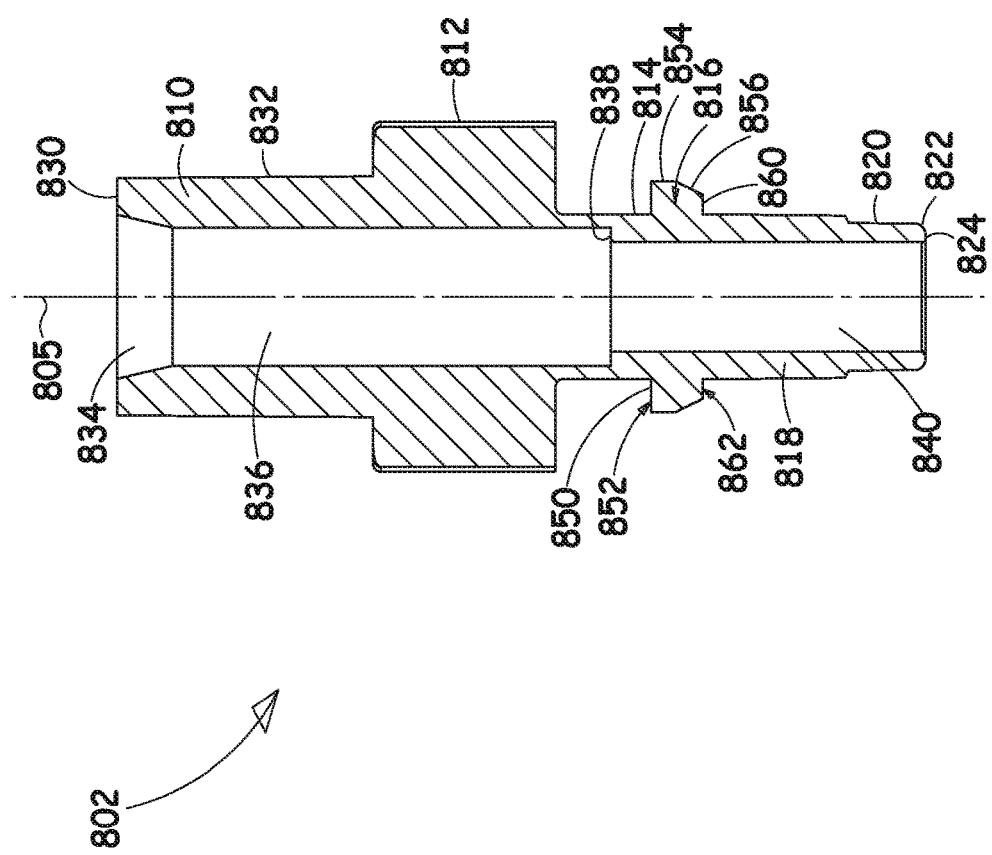

Reference is now additionally made to FIGS. 9A and 9B, which are simplified respective pictorial sectional and plan view sectional illustrations of base element 802.

As seen in FIGS. 8A-9B, base element 802 is preferably an integrally formed element, injection molded of plastic and includes a generally cylindrical end portion 810, a splined generally cylindrical intermediate portion 812, arranged for being gripped by a user's fingers, a first generally circular cylindrical intermediate portion 814, a flange portion 816, a second generally circular cylindrical intermediate portion 818, a third generally circular cylindrical intermediate portion 820 and a rounded portion 822, terminating in a generally circular ring end surface 824.

As seen particularly in FIGS. 9A and 9B, generally cylindrical end portion 810 includes a generally circular ring end surface 830, which preferably lies in a plane perpendicular to a cylindrical outer surface 832 of generally cylindrical end portion 810. Generally cylindrical end portion 810 preferably includes an inwardly tapered inner surface 834, extending inwardly from generally circular ring end surface 830, and terminating in a first axial circular cylindrical bore 836. First axial circular cylindrical bore 836 extends through splined generally cylindrical intermediate portion 812 and partially into first generally circular cylindrical intermediate portion 814 and terminates at a shoulder 838. A second axial circular cylindrical bore 840, which has a diameter somewhat smaller than that of first axial circular cylindrical bore 836, extends from shoulder 838, through rounded portion 822 to generally circular ring end surface 824.

It is a particular feature of a preferred embodiment of the present invention that flange portion 816 is formed with a generally circular ring surface 850, which preferably lies in a plane perpendicular to first generally circular cylindrical intermediate portion 814 and defines a circumferential 90 degree shoulder 852 with respect thereto.

Flange portion 816 also defines a generally circular cylindrical surface 854, which extends from generally circular ring surface 850 to a generally circular tapered surface 856, which terminates at generally circular ring surface 860, which preferably lies in a plane perpendicular to second generally circular cylindrical intermediate portion 818 and defines a circumferential 90 degree shoulder 862 with respect thereto.

Preferably a tube, such as an IV line, is fixedly connected to base element 802 at first axial circular cylindrical bore 836 and is UV or heat welded thereto.

Figure 10A:
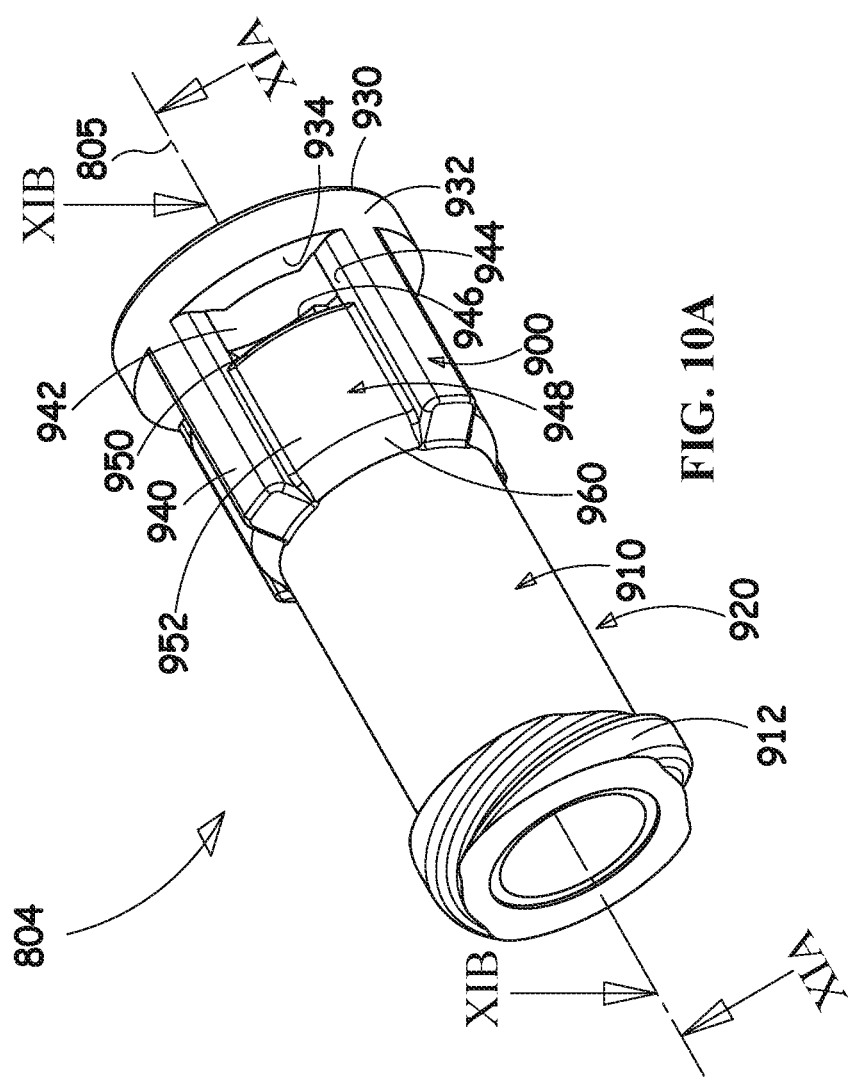
Figure 10D:
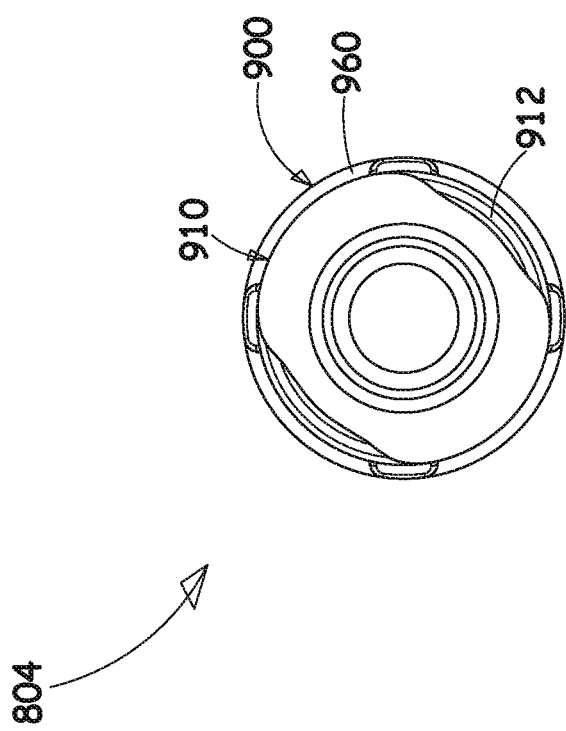
Figure 11B:
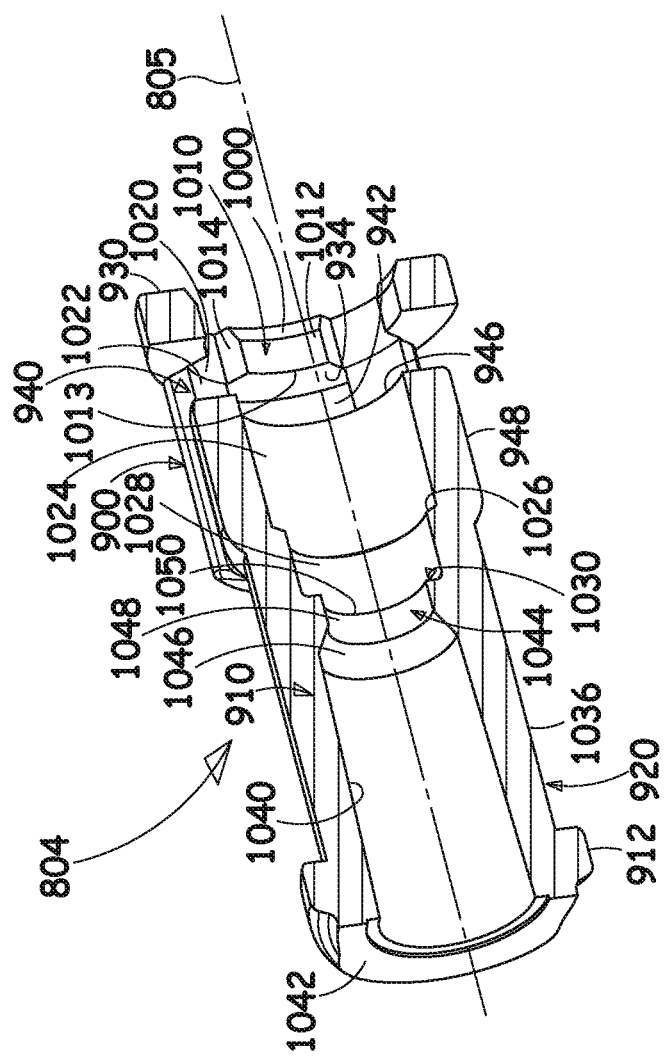

Reference is now made to FIGS. 10A, 10B, 10C and 10D, which are simplified respective pictorial, side view, first end view and second end view illustrations of rotating element 804, forming part of the fluid flow connector of FIGS. 8A and 8B, and to FIGS. 11A, 11B, 11C and 11D, which are, respectively, first and second pictorial sectional illustrations taken along respective lines XIA-XIA and XIB-XIB in FIG. 10A, and first and second plan view sectional illustrations taken along respective lines XIA-XIA and XIB-XIB in FIG. 10A.

As seen particularly in FIGS. 10A-10D, rotating element 804 is preferably an integrally formed generally circularly symmetric element arranged about longitudinal axis 805. Rotating element 804 is preferably injection molded of plastic and includes a first generally cylindrical portion 900, a second generally cylindrical portion 910, having an overall outer diameter which is less than that of first generally cylindrical portion 900 and an outer threaded end portion 912, wherein the second portion 910 and the outer threaded end portion 912 constitute a female luer connector portion 920.

First generally cylindrical portion 900 preferably includes a generally circular ring end surface 930 from which extends, about longitudinal axis 805, a generally circular cylindrical surface 932. It is a particular feature of an embodiment of the present invention that generally circular cylindrical surface 932 terminates at a generally circular broken ring surface 934, which is preferably parallel to generally circular ring end surface 930 and lies in a plane perpendicular to axis 805 and to generally circular cylindrical surface 932.

A plurality of mutually separated elongate portions 940, preferably four in number, extend from generally circular broken ring surface 934 towards second generally cylindrical portion 910 and define therebetween a plurality of windows 942, preferably four in number. Windows 942 are preferably each bounded by a portion of generally circular broken ring surface 934, by a pair of radially extending side surfaces 944 of adjacent elongate portions 940 and by a generally circular ring end surface 946 of a generally cylindrical portion 948. Generally circular ring end surface 946 preferably lies in a plane parallel to that of generally circular broken ring surface 934 and preferably defines a rounded circumferential corner edge 950 with a generally circular cylindrical outer surface 952 of generally cylindrical portion 948.

Generally circular cylindrical outer surface 952 extends from generally circular ring end surface 946 to a tapered generally circumferential surface 960, which extends, in turn to second generally cylindrical portion 910.

Referring now specifically to FIGS. 11A, 11B, 11C and 11D, it is seen that generally circular ring end surface 930 terminates radially inwardly in a plurality of tapered circumferential surfaces 1000, each formed on a radially inward edge of a corresponding window lintel portion 1010, extending between adjacent elongate portions 940. Each window lintel portion 1010 also includes a generally circular cylindrical radially inward facing surface portion 1012 and a pair of radially extending side wall portions 1014, all of which terminate at generally circular broken ring surface 934.

It is a particular feature of an embodiment of the present invention that the junction between radially inward facing surface portion 1012 and generally circular broken ring surface 934 defines a mutually perpendicular, generally circumferential shoulder 1013.

It is also seen that azimuthally intermediate window lintel portions 1010 there are defined generally circular cylindrical inwardly facing surface portions 1020, which extend into corresponding generally circular cylindrical inwardly facing surface portions 1022, which terminate at ring surface 946.

A first generally circularly symmetric inner facing bore surface 1024 extends through generally cylindrical portion 948 to a shoulder 1026, preferably 90 degrees, from which extends a second generally circularly symmetric inner facing bore surface 1028. Second generally circularly symmetric inner facing bore surface 1028 extends to a shoulder 1030, preferably 90 degrees, from which extends an interior bore of female luer connector portion 920.

Female luer connector portion 920 defines a generally cylindrical outer surface 1036 which extends from tapered surface 960 to outer threaded end portion 912. Female luer connector portion 920 includes an outwardly tapered bore 1040 having a chamfered opening edge 1042 and including an inwardly directed flange portion 1044 having a tapered circumferential edge 1046 which terminates in a generally cylindrical edge surface 1048 which terminates in a ring portion 1050, which lies in a plane perpendicular to axis 805 at shoulder 1030.

Figure 12A:
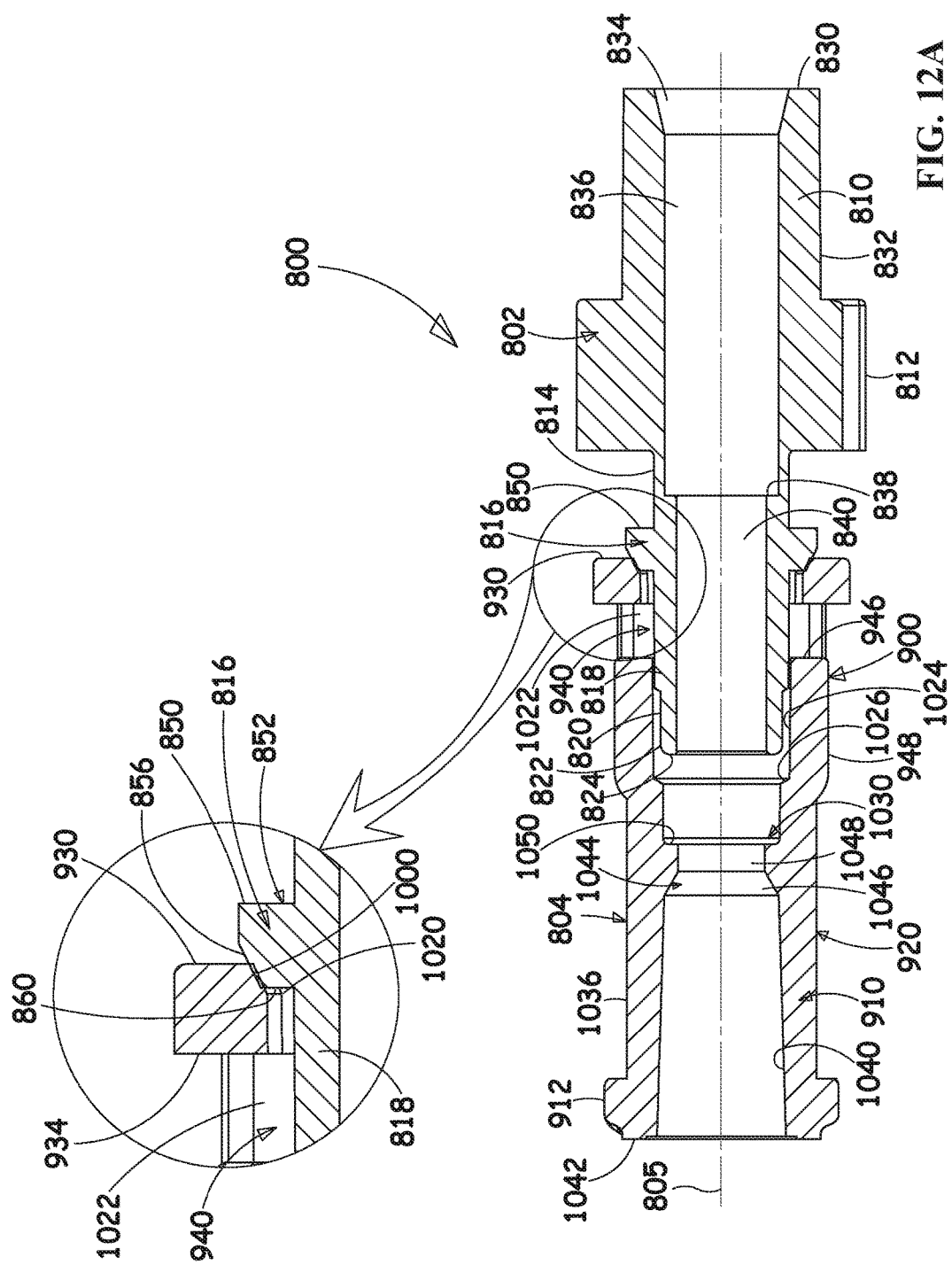
FIGS. 12A, 12B and 12C are simplified plan view sectional illustrations taken along lines XII-XII in FIG. 8A, which illustrate three stages in the assembly of the fluid flow connector of FIGS. 8A-11E.
Figure 12B:
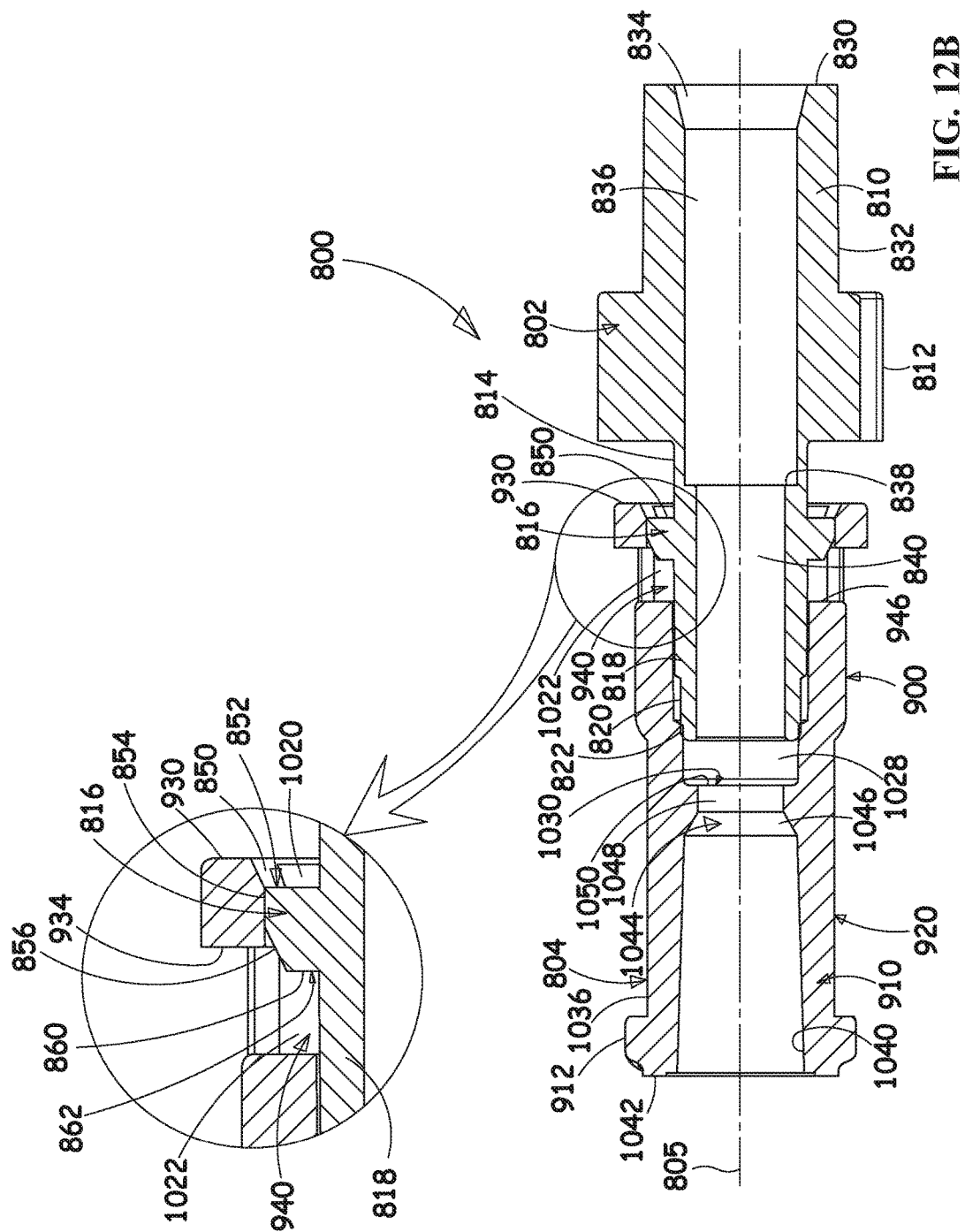
Figure 12C:
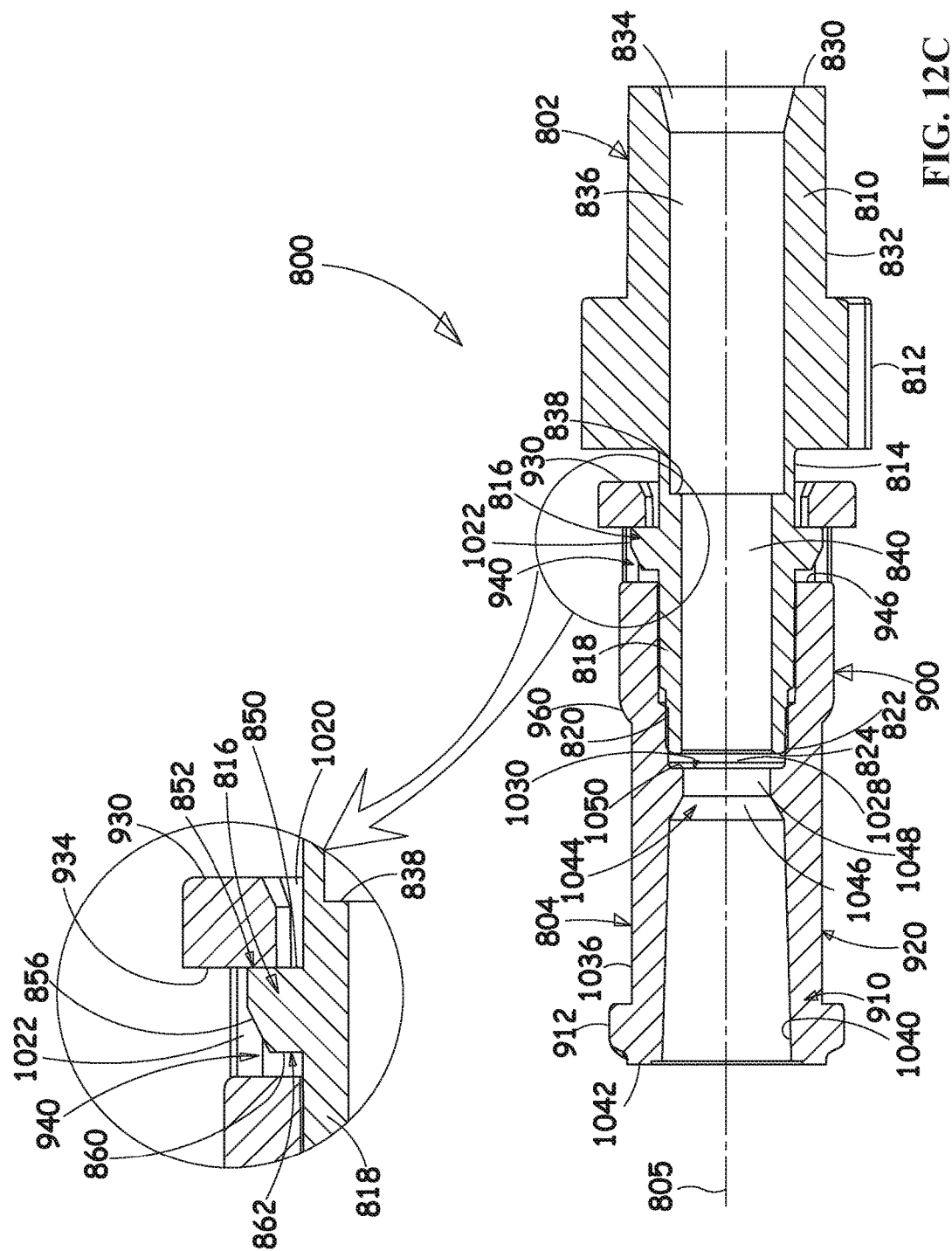
Figure 13A:
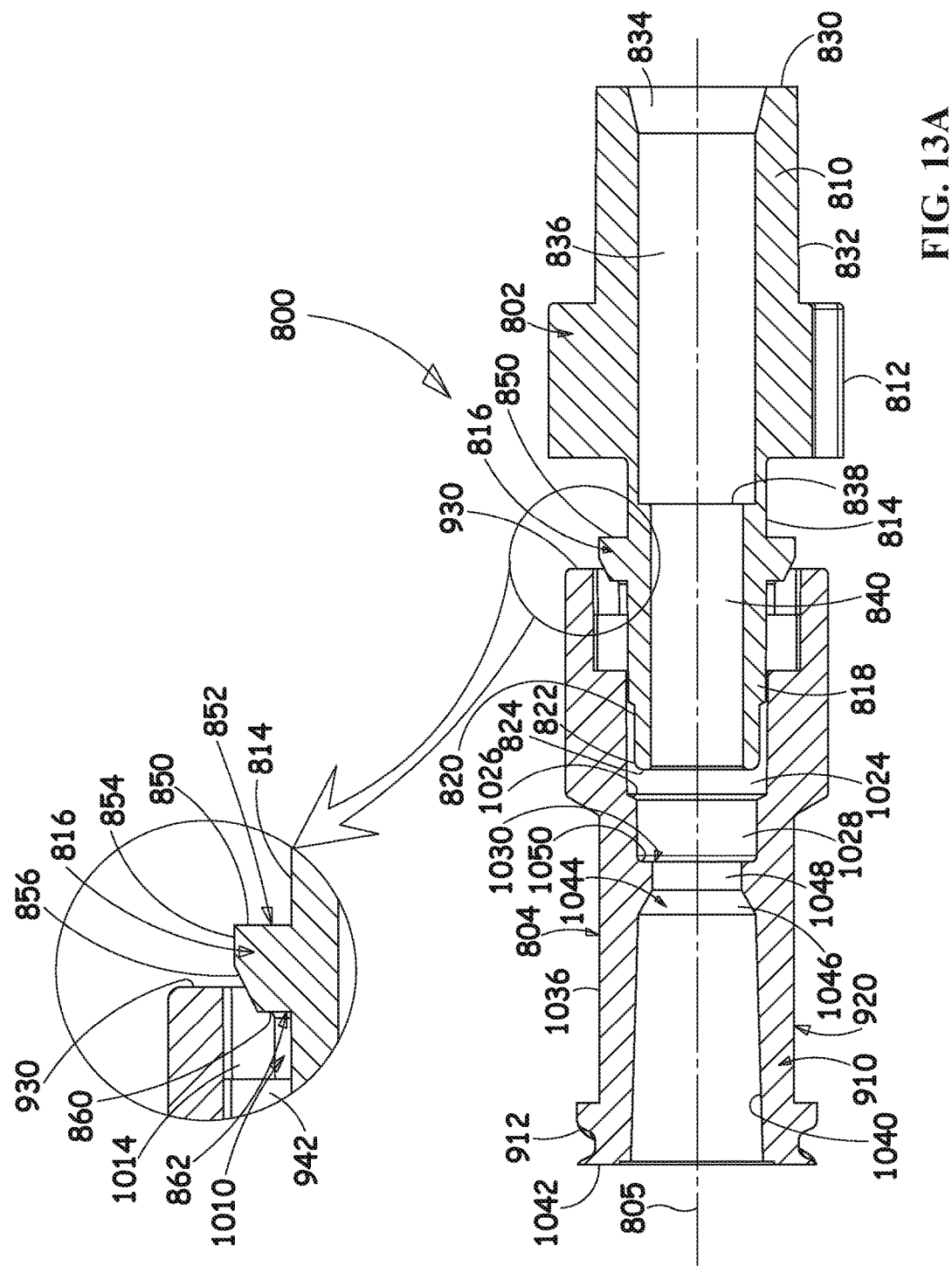
FIGS. 13A, 13B and 13C are simplified plan view sectional illustrations taken along lines XIII-XIII in FIG. 8A, which illustrate three stages in the assembly of the fluid flow connector of FIGS. 8A-11E.
Figure 13B:
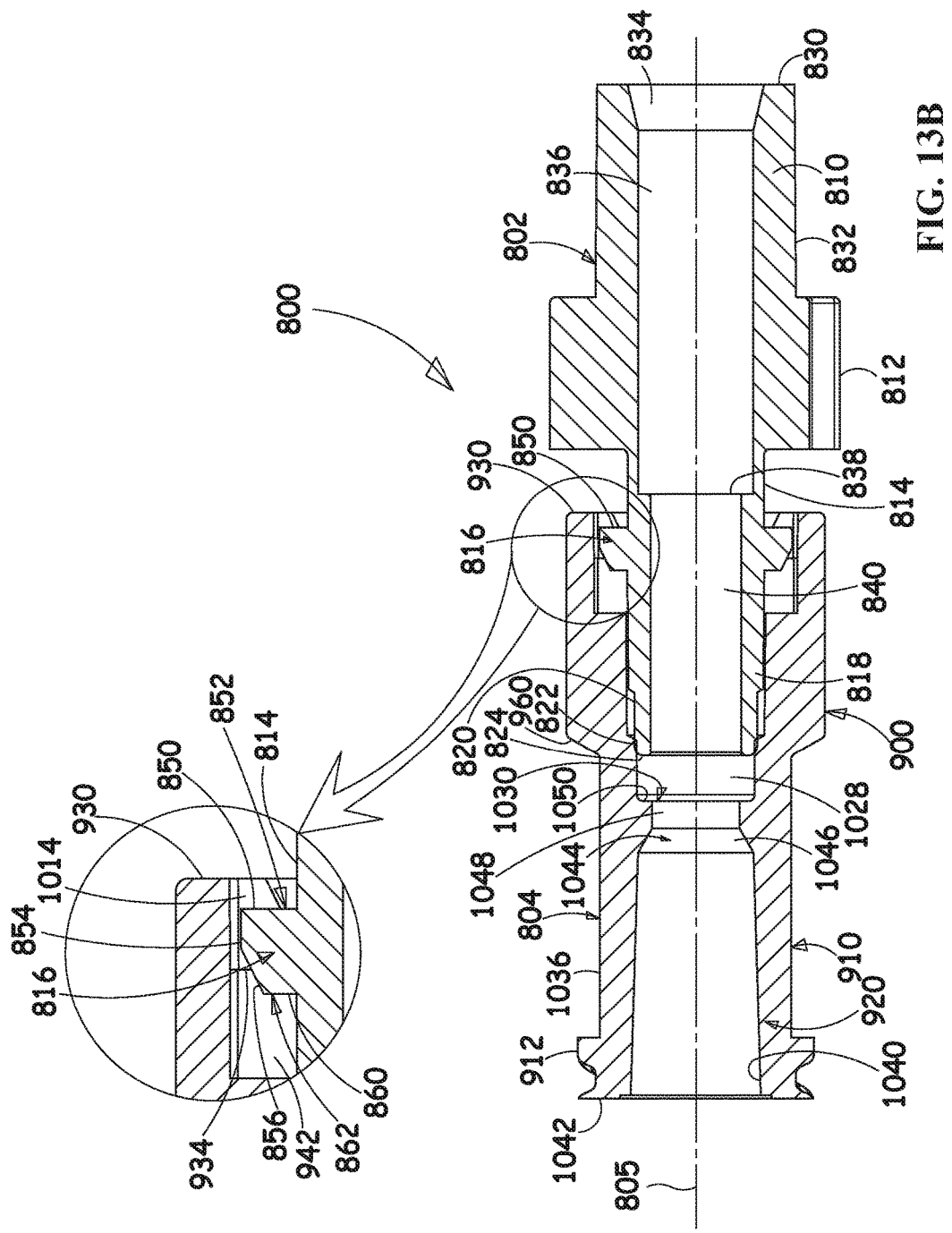
Figure 13C:
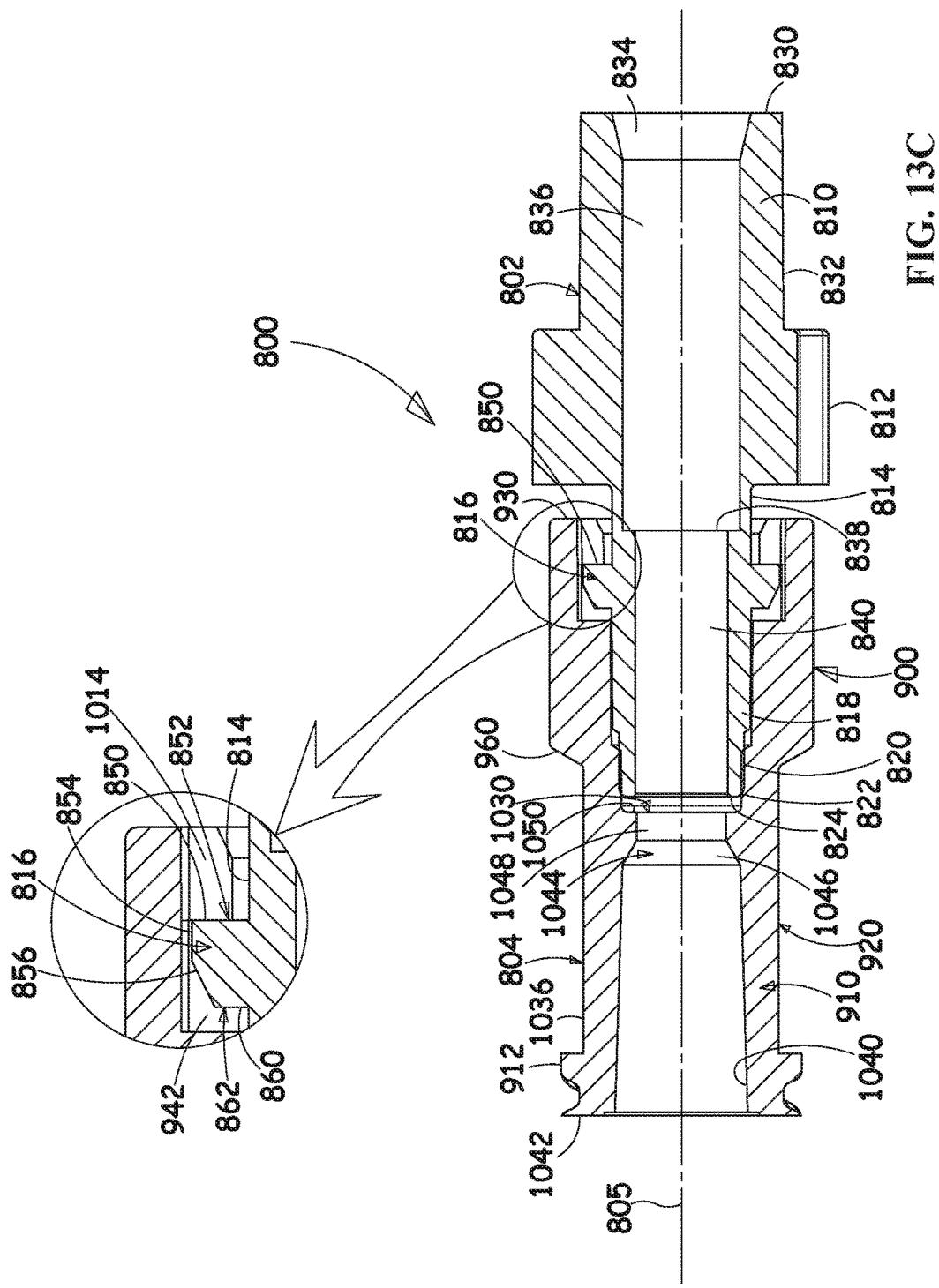

Reference is now made to FIGS. 12A, 12B and 12C, which are simplified plan view sectional illustrations taken along lines XII-XII in FIG. 8A, and to FIGS. 13A, 13B and 13C, which are simplified plan view sectional illustrations taken along lines XIII-XIII. FIGS. 12A-12C and FIGS. 13A-13C each illustrate the same three stages in the assembly of the fluid flow connector 800 of FIGS. 8A-11E.

Turning initially to FIGS. 12A and 13A, and particularly to FIG. 12A, it is seen that both base element 802 and rotating element 804 are arranged along mutual longitudinal axis 805. Tapered circumferential surfaces 1000 of rotating element 804 engage circular tapered surface 856 of flange portion 816 of base element 802. Second generally circular cylindrical intermediate portion 818 of base element 802 engages circularly symmetric inner facing bore surface 1024 of rotating element 804.

Turning now to FIGS. 12B and 13B, and particularly to FIG. 12B, it is seen that generally circular cylindrical radially inward facing surface portions 1012 of rotating element 804 engage generally circular cylindrical surface 854 of flange portion 816 of base element 802, thereby temporarily bending elongate portions 940 radially outwardly and temporarily stretching first generally cylindrical portion 900 at generally circular ring end surface 930 and circular cylindrical surface 932. Third generally circular cylindrical intermediate portion 820 of base element 802 engages second generally circularly symmetric inner facing bore surface 1028 of rotating element 804.

FIGS. 12C and 13C, particularly FIG. 12C, illustrate mutually rotatable, mutually axially locked engagement of rotating element 804 with base element 802, which is a particular feature of an embodiment of the present invention. It is seen that generally circular broken ring surface 934 of rotating element 804 rotatably engages generally circular ring surface 850 of base element 802 at shoulder 852, thereby locking rotating element 804 and base element 802 against mutual axial separation along axis 805. It is also seen that third generally circular cylindrical intermediate portion 820 of base element 802 engages second generally circularly symmetric inner facing bore surface 1028 of rotating element 804 at shoulder 1030, thereby limiting the axial distance along which rotating element 804 and base element 802 can approach each other along axis 805. It is also seen that elongate portions 940 are no longer bent radially outwardly and that first generally cylindrical portion 900 is no longer stretched at generally circular ring end surface 930 and circular cylindrical surface 932.

Figure 14A:
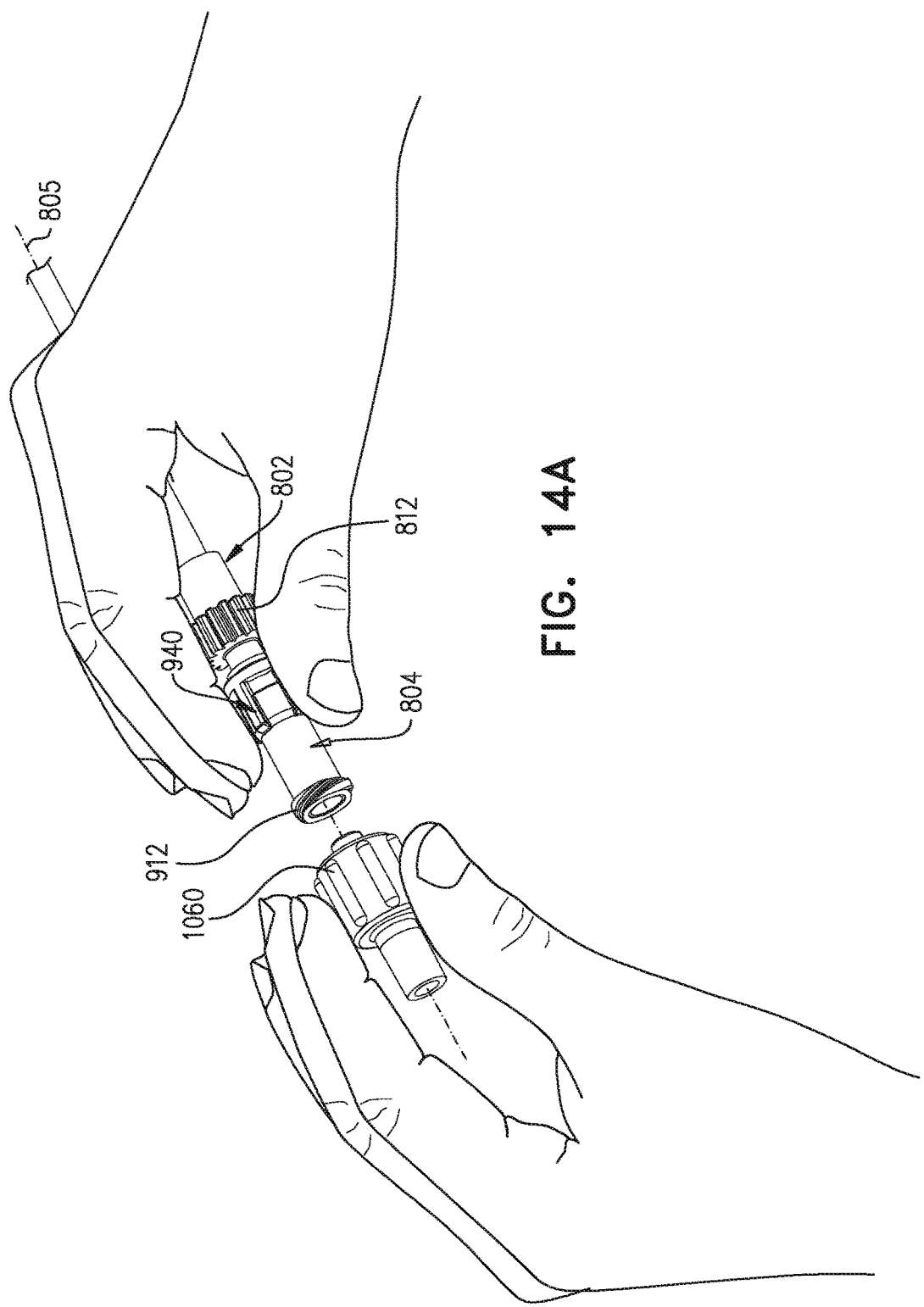
Figure 14B:
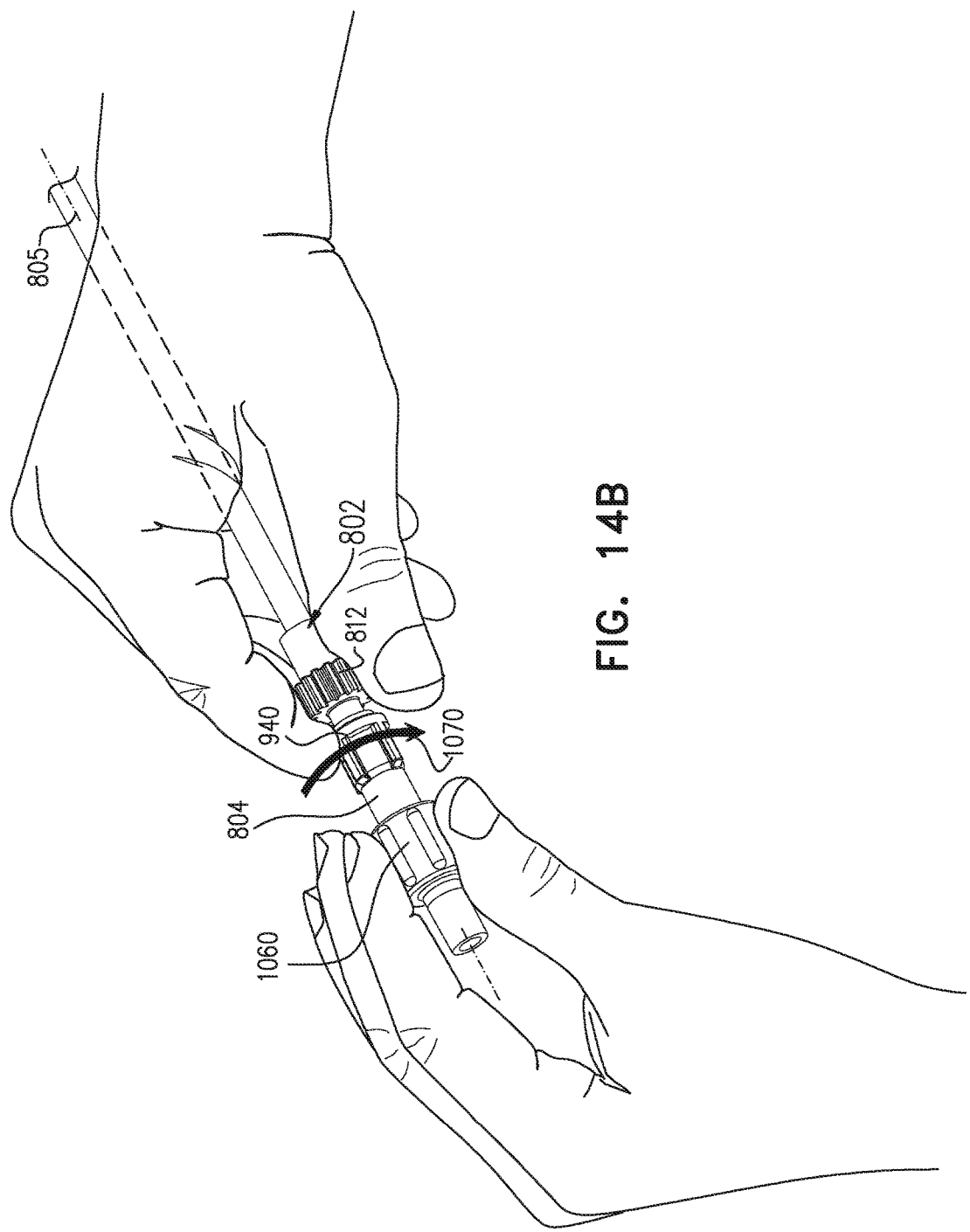

Reference is now made to FIGS. 14A, 14B and 14C, which are simplified pictorial illustrations of three stages of attaching a male luer connector to a rotating element forming part of the fluid flow connector of FIGS. 8A-13C, wherein a base element of the fluid flow connector is connected to a fluid flow conduit.

Turning initially to FIG. 14A, it is seen that a user holds rotating element 804, typically in the user's right hand, typically by gripping it at elongate portions 940 of first generally cylindrical portion 900, and holds a male luer connector 1060, typically in the user's left hand, mutually orienting the luer connector 1060 along longitudinal axis 805 of the joined base element 802 and rotating element 804.

Turning now to FIG. 14B, it is seen that the user, typically using the user's right hand, rotates the rotating element 804 in a direction indicated by an arrow 1070 by gripping elongate portions 940 of first generally cylindrical portion 900, thus threadably engaging an outwardly threaded surface 1072 of luer connector 1060 with luer threading 1050 of rotating element 804.

Turning now to FIG. 14C, it is seen that following threaded engagement of outwardly threaded surface 1072 of luer connector 1060 with luer threading 1050 of rotating element 804, the rotating element 804 may be freely rotated relative to the base element 802. This is illustrated by showing that the user holds base element 802 typically in the user's right hand, gripping it at splined generally cylindrical intermediate portion 812, while typically the user's left hand rotates the rotating element 804, as indicated by an arrow 1074.

It will be appreciated by persons skilled in the art that the present invention is not limited to what has been particularly described hereinabove and includes both combinations and subcombinations of features described hereinabove as well as variations and modifications thereof which would occur to persons skilled in the art upon reading the foregoing and which are not in the prior art.

The invention claimed is:

1. A rotatable fluid flow connector comprising:
   a base element; and
   a rotatable element,
   said rotatable element being non-removably but rotatably connected to
   said base element for rotation about a common axis at all times and wherein said rotatable element and said base element are mutually axially locked.

2. A rotatable fluid flow connector according to claim 1 and wherein:
   one of said base element and said rotatable element is formed with a flange having at least one flange surface extending in a plane which is perpendicular to said common axis; and
   another of said base element and said rotatable element is formed with at least one flange engagement surface facing said at least one flange surface and extending in a plane which is perpendicular to said common axis.

3. A rotatable fluid flow connector according to claim 2 and wherein said base element is integrally formed with another connector.

4. A rotatable fluid flow connector according to claim 1 and wherein said base element is integrally formed with another connector.

5. A rotatable fluid flow connector according to claim 1 and wherein said base element adapted for a fixed, non-rotatable connection to a tube.

6. A rotatable fluid flow connector according to claim 1 and wherein said rotatable element is integrally formed with a male luer connector.

7. A rotatable fluid flow connector according to claim 1 and wherein said rotatable element is integrally formed with a female luer connector.

8. A rotatable fluid flow connector according to claim 1 and wherein said rotatable element at least partially surrounds a portion of said base element and said rotatable element comprises a plurality of elongate portions configured to temporarily bend radially outwardly to provide locking engagement between said rotating element and said base element.

9. A rotatable fluid flow connector according to claim 8 and wherein said locking engagement allows rotational movement of said rotatable element relative to said base element and limits axial separation between said rotating element and said base element.

10. A rotatable fluid flow connector according to claim 1 and wherein said rotatable element at least partially surrounds a portion of said base element and said rotatable element comprises a cylindrical portion configured to temporarily stretch radially outwardly to provide locking engagement between said rotating element and said base element.

11. A rotatable fluid flow connector according to claim 10 and wherein said locking engagement allows rotational movement of said rotatable element relative to said base element and limits axial separation between said rotating element and said base element.

12. For use in a rotatable fluid flow connector including a base element,
a rotatable element arranged for axial locking engagement with said base element and rotation with respect thereto about a common axis at all times, said rotatable element being formed with a flange having at least one flange surface extending in a plane which is perpendicular to said common axis.

13. A rotatable element for use in a rotatable fluid flow connector according to claim 12 and wherein said rotatable element is formed with at least one flange engagement surface extending in a plane which is perpendicular to said common axis and facing at least one flange surface formed on said base element and extending in a plane which is perpendicular to said common axis.

14. A rotatable element for use in a rotatable fluid flow connector according to claim 13 and wherein said rotatable element is integrally formed with a male luer connector.

15. A rotatable element for use in a rotatable fluid flow connector according to claim 12 and wherein said rotatable element is integrally formed with a male luer connector.

16. A rotatable element for use in a rotatable fluid flow connector according to claim 12 and wherein said rotatable element is integrally formed with a female luer connector.

17. A rotatable element for use in a rotatable fluid flow connector according to claim 12 and wherein said rotatable element comprises a plurality of elongate portions configured to temporarily bend radially outwardly to provide locking engagement between said rotatable element and said base element.

18. A rotatable element for use in a rotatable fluid flow connector according to claim 17 and wherein said locking engagement allows rotational movement of said rotatable element relative to said base element and limits axial separation between said rotating element and said base element.

19. A rotatable element for use in a rotatable fluid flow connector according to claim 12 and wherein said rotatable element comprises a cylindrical portion configured to temporarily stretch radially outwardly to provide locking engagement between said rotatable element and said base element.

20. A rotatable element for use in a rotatable fluid flow connector according to claim 19 and wherein said locking engagement allows rotational movement of said rotatable element relative to said base element and limits axial separation between said rotating element and said base element.

* * * * *